(12) United States Patent
Romoscanu

(10) Patent No.: US 9,795,765 B2
(45) Date of Patent: Oct. 24, 2017

(54) VARIABLE STIFFNESS STEERING MECHANISM FOR CATHETERS

(75) Inventor: Alexandre Romoscanu, Meyrin (CH)

(73) Assignee: St. Jude Medical International Holding S.à r.l., Luxembourg (LU)

(*) Notice: Subject to any disclaimer, the term of this patent is extended or adjusted under 35 U.S.C. 154(b) by 725 days.

(21) Appl. No.: 13/084,155

(22) Filed: Apr. 11, 2011

(65) Prior Publication Data

US 2011/0251519 A1    Oct. 13, 2011

Related U.S. Application Data

(60) Provisional application No. 61/322,627, filed on Apr. 9, 2010, provisional application No. 61/424,445, filed on Dec. 17, 2010.

(51) Int. Cl.
*A61M 25/01* (2006.01)
*A61M 25/00* (2006.01)
*A61B 1/00* (2006.01)
*A61B 1/005* (2006.01)

(52) U.S. Cl.
CPC .... *A61M 25/0147* (2013.01); *A61M 25/0013* (2013.01); *A61M 25/0053* (2013.01); *A61M 25/0054* (2013.01); *A61B 1/0055* (2013.01); *A61B 1/00078* (2013.01); *A61M 25/0051* (2013.01); *A61M 25/0052* (2013.01); *A61M 25/0138* (2013.01); *A61M 2025/0046* (2013.01); *A61M 2025/0059* (2013.01)

(58) Field of Classification Search
CPC .......... A61M 25/0013; A61M 25/0054; A61M 25/0147; A61M 25/0053; A61M 25/0051; A61M 25/0052; A61M 25/0138; A61M 2025/0059; A61M 2025/0046; A61B 1/00078; A61B 1/0055
USPC ............. 600/433–435, 585; 604/164.13
See application file for complete search history.

(56) References Cited

U.S. PATENT DOCUMENTS

| | | |
|---|---|---|
| 2,515,366 A | 7/1950 | Zublin |
| 3,416,531 A | 12/1968 | Edwards |
| 3,557,780 A | 1/1971 | Sato |
| 3,572,325 A | 3/1971 | Bazell et al. |
| 3,583,393 A | 6/1971 | Takahashi |
| 3,700,289 A | 10/1972 | Billinski et al. |
| 3,710,781 A | 1/1973 | Huthcins |
| 3,739,770 A | 6/1973 | Muri |
| 3,799,151 A | 3/1974 | Fukaumi et al. |
| 3,802,440 A | 4/1974 | Salem et al. |

(Continued)

*Primary Examiner* — Rene Towa
(74) *Attorney, Agent, or Firm* — Dykema Gossett PLLC

(57) ABSTRACT

A catheter assembly including a tapered steering spine having a varying stiffness along an axial length. The tapered steering spine is tailored to provide increasing flexibility from proximal to distal in a way that makes the bend radius more uniform along the length of the steering section. In one embodiment, the tapered steering spine includes structures on adjacent rings that engage with each other when the steering section is flexed to limit the minimum bend radius to a predetermined minimum and which enhances the torsional rigidity of the steering section regardless of the degree of flexure of the steering section. The limited bend radius can prevent excessive bending of components such as fiber optics. The enhanced torsional rigidity can negate the need for torque braid in the section of the catheter shaft that surrounds the tapered steering spine.

19 Claims, 11 Drawing Sheets

(56) References Cited

U.S. PATENT DOCUMENTS

| | | |
|---|---|---|
| 3,905,361 A | 9/1975 | Hewson et al. |
| 3,948,255 A | 4/1976 | Davidson |
| 3,998,216 A | 12/1976 | Hosono |
| 4,108,211 A | 8/1978 | Tanaka |
| 4,329,980 A | 5/1982 | Terada |
| 4,351,323 A | 9/1982 | Ouchi et al. |
| 4,432,349 A | 2/1984 | Oshiro |
| 4,502,482 A | 3/1985 | DeLuccia et al. |
| 4,516,972 A | 5/1985 | Samson |
| 4,543,090 A | 9/1985 | McCoy |
| 4,580,551 A | 4/1986 | Siegmund et al. |
| 4,586,923 A | 5/1986 | Gould et al. |
| 4,601,705 A | 7/1986 | McCoy |
| 4,612,927 A | 9/1986 | Krüger |
| 4,664,113 A | 5/1987 | Frisbie et al. |
| 4,700,693 A | 10/1987 | Lia et al. |
| 4,723,936 A | 2/1988 | Buchbinder et al. |
| 4,753,223 A | 6/1988 | Bremer |
| 4,771,788 A | 9/1988 | Millar |
| 4,834,069 A | 5/1989 | Umeda |
| 4,850,351 A | 7/1989 | Herman et al. |
| 4,874,371 A | 10/1989 | Comben et al. |
| 4,886,067 A | 12/1989 | Palermo |
| 4,898,577 A | 2/1990 | Badger et al. |
| 4,940,062 A | 7/1990 | Hampton et al. |
| 4,960,134 A | 10/1990 | Webster |
| 4,960,410 A | 10/1990 | Pinchuk |
| 4,960,411 A | 10/1990 | Buchbinder |
| 4,998,916 A | 3/1991 | Hammerslag et al. |
| 4,998,923 A | 3/1991 | Samson et al. |
| 5,030,204 A | 7/1991 | Badger et al. |
| 5,056,517 A | 10/1991 | Fenici |
| 5,108,368 A | 4/1992 | Hammerslag et al. |
| 5,114,414 A | 5/1992 | Buchbinder |
| 5,125,895 A | 6/1992 | Buchbinder et al. |
| 5,152,744 A | 10/1992 | Krause et al. |
| 5,178,129 A | 1/1993 | Chikama et al. |
| 5,190,050 A | 3/1993 | Nitzsche |
| 5,228,441 A | 7/1993 | Lundquist |
| 5,242,430 A | 9/1993 | Arenas et al. |
| 5,299,562 A | 4/1994 | Heckele et al. |
| 5,304,131 A | 4/1994 | Paskar |
| 5,315,996 A | 5/1994 | Lundquist |
| 5,318,525 A | 6/1994 | West et al. |
| 5,322,064 A | 6/1994 | Lundquist |
| 5,329,923 A | 7/1994 | Lundquist |
| 5,358,479 A | 10/1994 | Wilson |
| 5,364,351 A | 11/1994 | Heinzelman et al. |
| 5,368,564 A | 11/1994 | Savage |
| 5,383,852 A | 1/1995 | Stevens-Wright |
| 5,383,923 A | 1/1995 | Webster, Jr. |
| 5,394,864 A | 3/1995 | Kobayashi et al. |
| 5,395,327 A | 3/1995 | Lundquist et al. |
| 5,395,328 A | 3/1995 | Ockuly et al. |
| 5,397,304 A | 3/1995 | Truckai |
| 5,409,000 A | 4/1995 | Imran |
| 5,431,168 A | 7/1995 | Webster, Jr. |
| 5,437,288 A | 8/1995 | Schwartz et al. |
| 5,441,483 A | 8/1995 | Avitall |
| 5,448,989 A | 9/1995 | Heckele |
| 5,454,787 A | 10/1995 | Lundquist |
| 5,456,664 A | 10/1995 | Heinzelman et al. |
| 5,462,527 A | 10/1995 | Stevens-Wright et al. |
| 5,477,856 A | 12/1995 | Lundquist |
| 5,478,330 A | 12/1995 | Imran et al. |
| 5,484,407 A | 1/1996 | Osypka |
| 5,487,757 A | 1/1996 | Truikai et al. |
| 5,507,725 A | 4/1996 | Savage et al. |
| 5,531,686 A | 7/1996 | Lundquist et al. |
| 5,545,200 A | 8/1996 | West et al. |
| 5,562,619 A | 10/1996 | Mirarchi et al. |
| 5,573,520 A | 11/1996 | Schwartz et al. |
| 5,603,697 A | 2/1997 | Grundy et al. |
| 5,605,543 A | 2/1997 | Swanson |
| 5,611,777 A | 3/1997 | Bowden et al. |
| 5,656,029 A | 8/1997 | Imran et al. |
| 5,676,653 A | 10/1997 | Taylor et al. |
| 5,685,868 A | 11/1997 | Lundquist |
| 5,702,433 A | 12/1997 | Taylor et al. |
| 5,715,817 A | 2/1998 | Stevens-Wright et al. |
| 5,728,144 A | 3/1998 | Edwards et al. |
| 5,741,429 A | 4/1998 | Donadio, III et al. |
| 5,743,876 A | 4/1998 | Swanson |
| 5,749,828 A | 5/1998 | Solomon et al. |
| 5,779,669 A | 7/1998 | Haissaguerre et al. |
| 5,782,239 A | 7/1998 | Webster, Jr. |
| 5,782,828 A | 7/1998 | Chen et al. |
| 5,797,842 A | 8/1998 | Pumares et al. |
| 5,797,905 A | 8/1998 | Fleischman et al. |
| 5,807,241 A | 9/1998 | Heimberger |
| 5,820,591 A | 10/1998 | Thompson et al. |
| 5,824,031 A | 10/1998 | Cookston et al. |
| 5,833,632 A | 11/1998 | Jacobsen et al. |
| 5,857,046 A | 1/1999 | Barkus et al. |
| 5,865,800 A | 2/1999 | Mirarchi et al. |
| 5,881,727 A | 3/1999 | Edwards |
| 5,882,333 A | 3/1999 | Schaer et al. |
| 5,897,529 A | 4/1999 | Ponzi |
| 5,897,554 A | 4/1999 | Chia et al. |
| 5,904,667 A | 5/1999 | Falwell |
| 5,910,129 A | 6/1999 | Koblish et al. |
| 5,911,720 A | 6/1999 | Bourne et al. |
| 5,916,214 A | 6/1999 | Cosio et al. |
| 5,931,811 A | 8/1999 | Haissaguerre et al. |
| 5,935,102 A | 8/1999 | Bowden et al. |
| 5,944,690 A | 8/1999 | Falwell et al. |
| 5,967,978 A | 10/1999 | Littmann et al. |
| 6,004,279 A | 12/1999 | Crowley et al. |
| 6,027,473 A | 2/2000 | Ponzi |
| 6,027,863 A | 2/2000 | Donadio, III |
| 6,033,394 A | 3/2000 | Vidlund et al. |
| 6,048,339 A | 4/2000 | Zirps et al. |
| 6,063,080 A | 5/2000 | Nelson et al. |
| 6,096,036 A | 8/2000 | Bowe et al. |
| 6,107,004 A | 8/2000 | Donadio, III |
| 6,120,520 A | 9/2000 | Saadat et al. |
| 6,156,034 A | 12/2000 | Cosio et al. |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,221,070 B1 | 4/2001 | Tu et al. |
| 6,224,587 B1 | 5/2001 | Gibson |
| 6,241,728 B1 | 6/2001 | Gaiser et al. |
| 6,251,104 B1 | 6/2001 | Kesten et al. |
| 6,254,568 B1 | 7/2001 | Ponzi |
| 6,267,746 B1 | 7/2001 | Bumbalough |
| 6,270,496 B1 | 8/2001 | Bowe et al. |
| 6,428,489 B1 | 8/2002 | Jacobsen et al. |
| 6,440,088 B1 | 8/2002 | Jacobsen et al. |
| 6,468,260 B1 | 10/2002 | Bumbalough et al. |
| 6,470,205 B2 | 10/2002 | Bosselmann et al. |
| 6,500,167 B1 | 12/2002 | Webster, Jr. |
| 6,511,471 B2 * | 1/2003 | Rosenman et al. ........... 604/528 |
| 6,522,933 B2 | 2/2003 | Nguyen |
| 6,533,783 B1 | 3/2003 | Töllner |
| 6,551,271 B2 | 4/2003 | Nguyen |
| 6,569,114 B2 | 5/2003 | Ponzi et al. |
| 6,571,131 B1 | 5/2003 | Nguyen |
| 6,582,430 B2 | 6/2003 | Hall |
| 6,585,717 B1 | 7/2003 | Wittenberger et al. |
| 6,585,718 B2 | 7/2003 | Hayzelden et al. |
| 6,602,278 B1 | 8/2003 | Thompson et al. |
| 6,641,528 B2 | 11/2003 | Torii |
| 6,758,830 B1 | 7/2004 | Schaer et al. |
| 6,776,765 B2 | 8/2004 | Soukup et al. |
| 6,783,510 B1 | 8/2004 | Gibson et al. |
| 6,837,867 B2 | 1/2005 | Kortelling |
| 6,866,662 B2 | 3/2005 | Fuimaono et al. |
| 6,890,329 B2 | 5/2005 | Carroll et al. |
| 6,893,436 B2 | 5/2005 | Woodard et al. |
| 6,913,594 B2 | 7/2005 | Coleman et al. |
| 6,926,669 B1 | 8/2005 | Stewart et al. |
| 7,008,401 B2 | 3/2006 | Thompson et al. |

(56) References Cited

U.S. PATENT DOCUMENTS

| | | |
|---|---|---|
| 7,011,655 B2 | 3/2006 | Thompson et al. |
| 7,099,717 B2 | 8/2006 | Woodard et al. |
| 7,232,422 B2 | 6/2007 | Gibson et al. |
| 7,285,108 B2 | 10/2007 | Koerner et al. |
| 7,300,438 B2 | 11/2007 | Falwell et al. |
| 7,301,131 B2 | 11/2007 | Gauthier et al. |
| 7,331,958 B2 | 2/2008 | Falwell et al. |
| 7,344,543 B2 | 3/2008 | Sra |
| 7,371,232 B2 | 5/2008 | Scheib |
| 7,387,626 B2 | 6/2008 | Edwards et al. |
| 7,387,630 B2 | 6/2008 | Mest |
| 7,402,151 B2 | 7/2008 | Rosenmann et al. |
| 7,415,300 B2 | 8/2008 | Anderson et al. |
| 7,465,300 B2 | 12/2008 | Arless et al. |
| 7,524,301 B2 | 4/2009 | Dubois et al. |
| D599,904 S | 9/2009 | Anderson |
| 7,625,617 B1 | 12/2009 | Anderson et al. |
| 7,629,015 B2 | 12/2009 | Anderson et al. |
| 7,824,345 B2 | 11/2010 | Euteneuer et al. |
| 7,881,769 B2 | 2/2011 | Sobe |
| 7,914,466 B2 | 3/2011 | Davis et al. |
| 2004/0133220 A1* | 7/2004 | Lashinski et al. ............ 606/151 |
| 2008/0306467 A1* | 12/2008 | Reydel .......................... 604/523 |
| 2009/0018565 A1* | 1/2009 | To et al. ....................... 606/159 |
| 2009/0036833 A1* | 2/2009 | Parins ...................... 604/164.13 |
| 2009/0043283 A1* | 2/2009 | Turnlund et al. ............. 604/523 |
| 2009/0062871 A1* | 3/2009 | Chin et al. ................... 606/86 R |
| 2009/0182416 A1* | 7/2009 | Forster et al. ............... 623/2.11 |
| 2010/0152574 A1 | 6/2010 | Erdman et al. |
| 2010/0174269 A1* | 7/2010 | Tompkins et al. ............ 604/507 |

\* cited by examiner

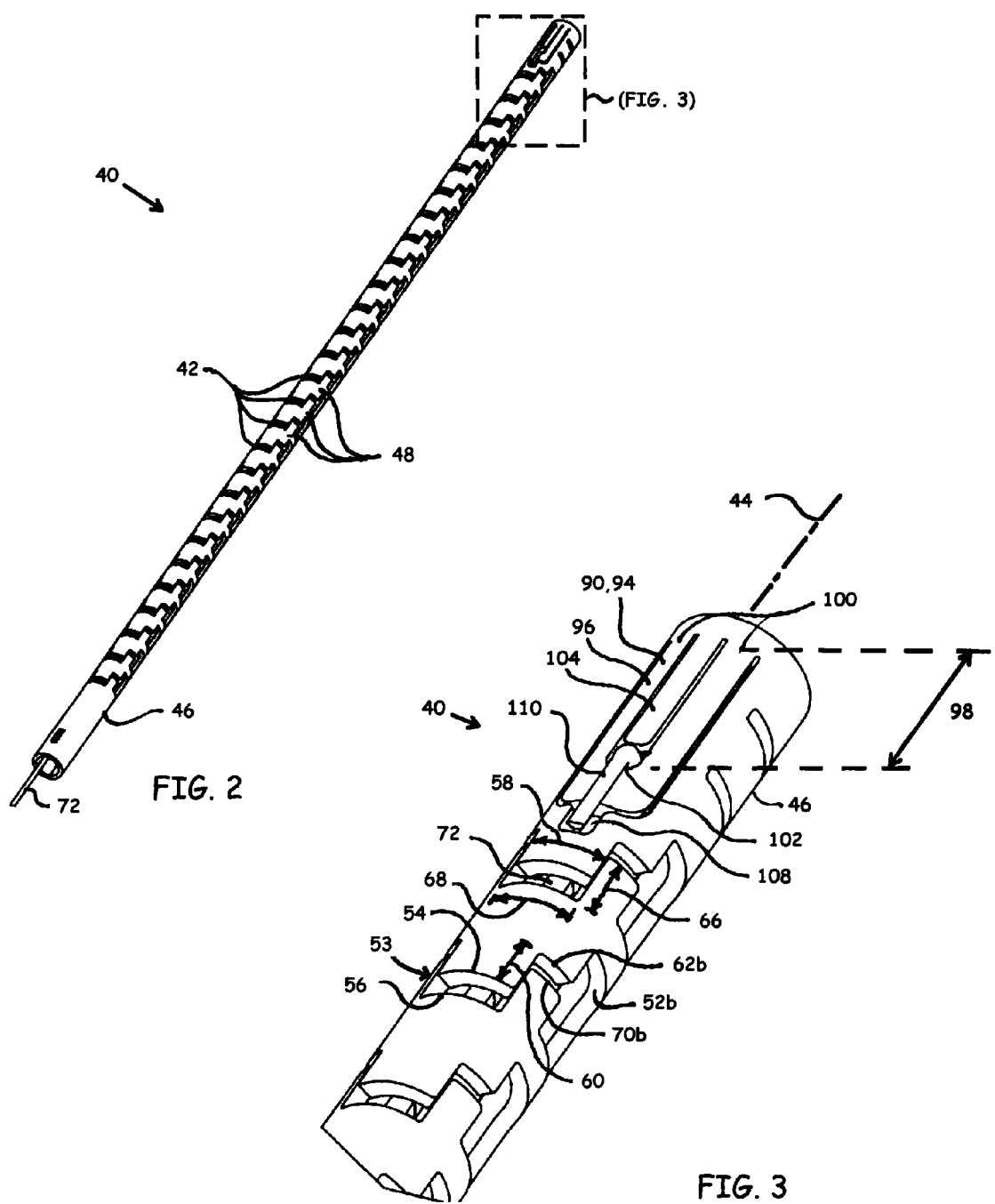

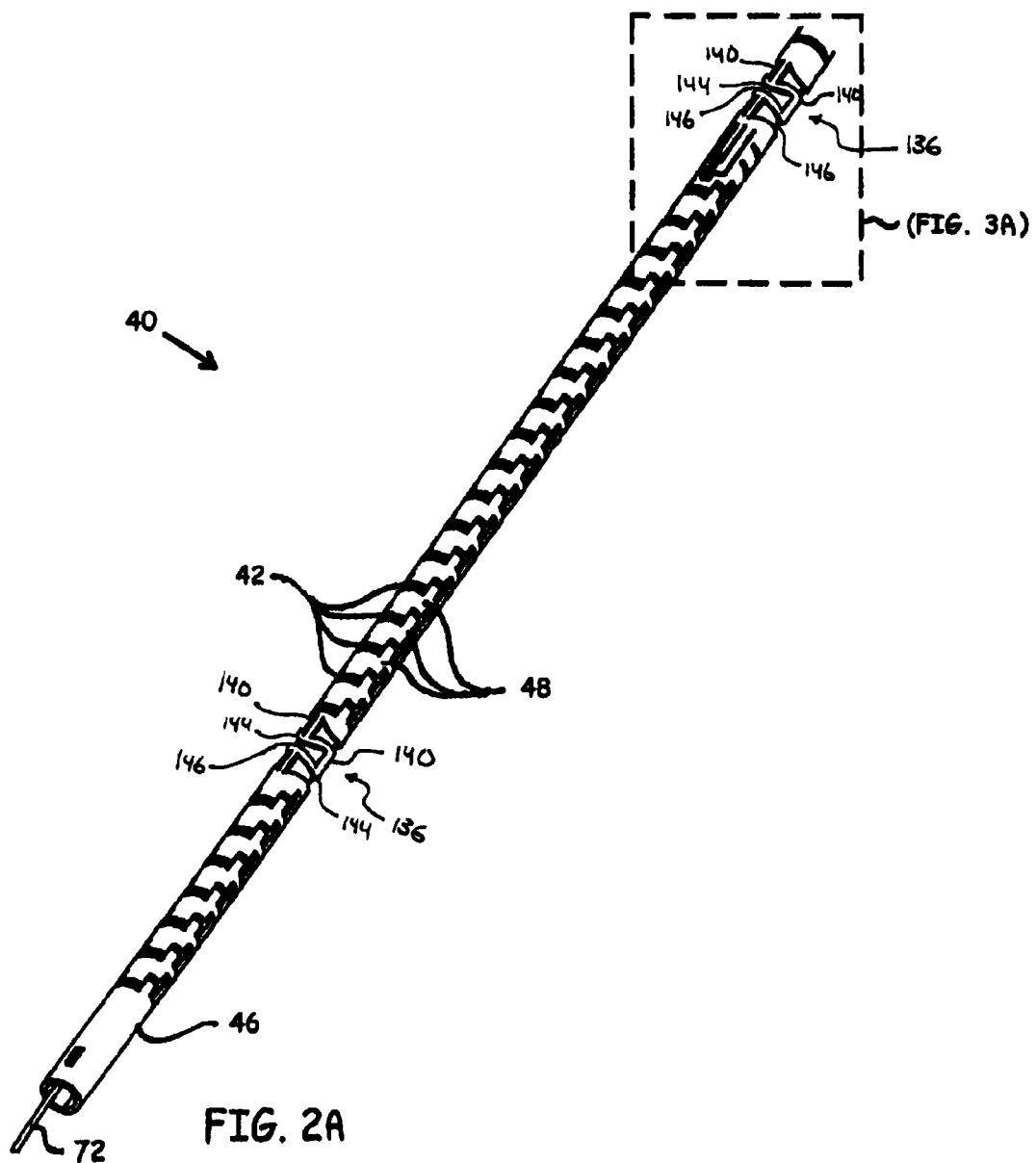

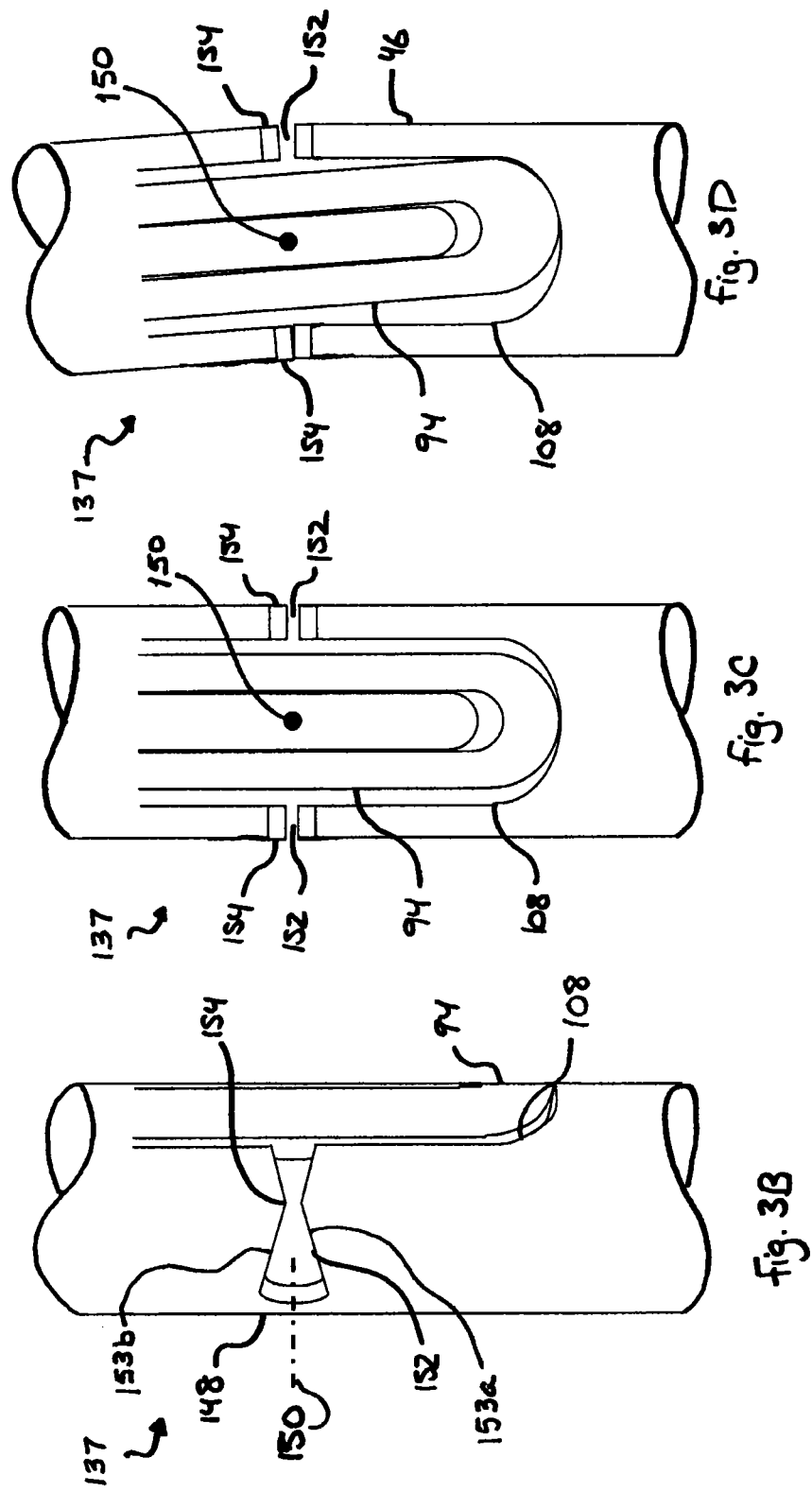

VARIABLE STIFFNESS STEERING
MECHANISM FOR CATHETERS

RELATED APPLICATIONS

This application claims the benefit of U.S. Provisional Patent Application No. 61/322,627, filed on Apr. 9, 2010, and U.S. Provisional Patent Application No. 61/424,445, filed on Dec. 17, 2010, the disclosures of which are hereby incorporated by reference herein in their entirety.

FIELD OF THE INVENTION

The invention relates generally to a steerable ablation catheter system with a deflectable catheter tip for navigating through biological lumen. More specifically, the invention is directed to a high-torque catheter with a deflectable tip section comprised of a tapered steering spine.

BACKGROUND

Catheters are widely used to reach a desired site within the circulatory system of a patient, such as the heart and adjacent arteries, to perform diagnostic or therapeutic medical procedures. Such catheters utilize a variety of designs to suit the requirements of specific medical procedures. In many cases, these catheters provide significant torsional rigidity while retaining sufficient longitudinal flexibility and stiffness. Accordingly, a wide array of devices address these needs, including various guidewires and steering spines.

For example, guidewires having variable stiffness along the length are known in the art, where the highest degree of flexibility is generally located at the distal end. Some past disclosures, such as U.S. Pat. Nos. 5,743,876 and 5,605,543 set forth guidewires and guidewire tubes with slots or perforations of uniform shape and dimension to provide flexibility. These references disclose axial spacing between the slots that varies along the length of a guidewire tube, with spacing closer at the distal end than at the proximal end. This arrangement made the guidewire more flexible at the distal end than at the proximal end. Other guidewire designs, such as U.S. Pat. No. 5,437,288 to Schwartz, use a pattern of grooves having increasing radial depth as the pattern approaches the distal tip, thus similarly providing a greater flexibility at the distal portion of the pattern than at the proximal portion of the pattern.

Steering spines represent another category of prior art catheter devices developed to provide certain flexibility and torsional characteristics. Steering spines are generally characterized by a continuous "spine" portion that extended the length of the steering mechanism. U.S. Pat. No. 5,685,868 to Lundquist describes an example of a steering spine. In some devices, this configuration was embodied by a slotted tube having a continuous spine portion along one side. Because the spine is the only continuous member that extended the length of the steering mechanism, it is the only member that can transmit torque. Some prior art devices, like the one described in U.S. Pat. No. 6,890,329 to Carroll et al, limit the minimum bend radius of the catheter as well.

Furthermore, a number of steering spines of variable stiffness and enhanced flexibility at the distal tip are found in the prior art. U.S. Pat. No. 6,776,765 to Soukup discloses a stylet wire having a lumen and a pull wire positioned within the lumen with the distal end portion of the pull wire secured to the stylet wire proximate the distal end portion of stylet wire. The stylet wire further includes notches that alter the strength of the wall of the stylet wire in the distal region. These notches allow the stylet wire to more easily bend when the relative tension force is applied between the stylet wire and the pull wire. In some embodiments, the radial depth of the notches are progressively increased from proximal to distal to accomplish the strength alteration.

Other steering spines of variable stiffness, such as disclosed in U.S. Pat. No. 5,507,725, include a strengthening member with diametrically opposed struts extending between ring structures. The struts can be tapered to achieve the desired flexing profile. Other steering spine designs, such as disclosed by U.S. Pat. No. 5,304,131 to Paskar, utilize a tube with crescent-shaped slots formed on one side. Paskar discloses the radial depth of the slots as increasing from proximal to distal along the axis of the steering spine, causing the tube to preferentially bend first at the gap with the greatest depth (i.e. the distal-most gap), and next at the gap with the second greatest depth, and finally at the gap with the least depth when tension is applied to the pull wire. The crescent shape enhances the torsional rigidity of the tube when the tube is bent so that the gaps are closed.

Other steering devices implement helically wound ribbons within a unitary structure to give the catheter torsional rigidity for turning and steering as the catheter is inserted, for example, into a biological lumen or other body passage. See U.S. Pat. No. 4,516,972 to Samson. The stiffness and torsional rigidity of the catheter can be varied along the length by varying the pitch of the helical wound ribbons. U.S. Pat. No. 3,802,440 to Salem, et al., discloses an introducer in which the extreme distal portion has a degree of curvature greater than that of the remainder of the distal portion. This result is achieved by increasing the depth and lateral length of the more distal slots in the tube member relative to the more proximal slots. Salem further discloses enhancement of the effect by varying the spacing between the slots. A combination of greater slot depth, greater slot length and closer slot spacing can be used to increase flexibility.

Segmented steering mechanisms are also known in the prior art. Segmented steering mechanisms are different from steering spine mechanisms in several ways. Unlike steering spine mechanisms, segmented steering mechanisms are not "unitary bodies" because there is no continuous portion that extends the length of the mechanism. Accordingly, while segmented steering mechanism can be formed from a unitary body, they are not unitary after formation, and thus lack the resiliency of a unitary body. Therefore, segmented steering mechanisms require additional structure to control bending, such as a second pull wire. Also, segmented steering mechanisms generally rely on structure between adjacent segments, such as the pivots, to translate torque. See U.S. Pat. No. 5,749,828 to Solomon et al. and U.S. Pat. No. 5,807,241 to Heimburger as examples of devices having segmented steering mechanisms.

Despite significant disclosures of catheter designs found in the prior art, new and improved designs continue to be desired which could provide improved flexibility and better accommodate the torque imposed during certain procedures.

It is therefore desired to provide a catheter apparatus with a deflectable tip section, such as a steering spine, that can accommodate significant torque, allow considerable flexibility, and provide an improved and more uniform bend radius along the length of the steering spine.

SUMMARY OF THE INVENTION

Various embodiments of the invention include a high-torque catheter shaft with a deflectable tip section comprising a tapered steering spine. The tapered steering spine is of variable flexibility, with the flexibility increasing from the proximal end to the distal end. The variable flexibility can be tailored to compensate for frictional losses between the steering spine and the plurality of cables and elongate accessories along the length of the tapered steering spine that can cause the tapered steering spine to bend non-uniformly in operation. Such cables and elongate accessories may include a pull wire, fiber optic, power lead, thermocouple, or irrigation tube, for example. Further, methods are disclosed that enable the tapering of the spine to compensate for the frictional losses so that there is a more uniform bend radius along the length of the tapered steering spine.

The prior art generally provides a bend radius that is irregular and that is not always conducive to the necessary catheter performance requirements. For example, with catheters that implement fiber optics, locally reduced bend radii generally causes a loss of light locally because of an effective reduction in the critical angle between the core fiber and the cladding. The loss of light leads to reduced sensitivity to detected strain due to loss of signal.

Also, an excessively small local bend radius presents the risk of over-flexing the fiber optics and causing them to break. A typical and non-limiting range of diameters of the fiber optics is from 50 µm to 250 µm, with standard industry fiber optics having diameters of 125 µm or greater. While fiber optics of greater diameter can provide the advantage of availability and reduced cost, there are advantages to implementing fiber optics having smaller diameters (i.e. less than 125 µm) that make the cost tradeoff more worthwhile. These advantages include more available space within the catheter shaft for other implements (leading to less friction between components), more sensitivity (i.e. greater strain per unit of applied force), and less resistance force to bending of the catheter shaft.

However, smaller diameter fiber optics are also more fragile than larger diameter fiber optics. Hence, controlling the bend radius in the steering section becomes a consideration generally, but in particular with respect to the viability of smaller diameter fiber optics.

A solution to these problems is to promote a uniform bending radius along the length of the steering spine that substantially minimizes the effect of local stresses and local loss of light from due to locally reduced bending radius. Accordingly, a uniform bend radius enables maximization or near maximization of catheter tip flexibility without compromising the performance or integrity of internal components such as fiber optics.

Other designs lack the necessary torsional strength for some applications, have increased profile dimensions, are difficult to manufacture, and/or do not provide the maneuverability sought by operators.

In order to address these and other needs, various embodiments of the invention include a high-torque catheter shaft with a deflectable tip section comprising a tapered steering spine. The tapered steering spine is of variable flexibility, with the flexibility increasing from the proximal end to the distal end. The variable flexibility can be tailored to compensate for frictional losses between the steering spine and plurality of cables and elongate accessories along the length of the tapered steering spine that can cause the tapered steering spine to bend non-uniformly in operation. Such cables and elongate accessories may include a pull wire, fiber optic, power lead, thermocouple, or irrigation tube, for example. A method is disclosed that enables the tapering of the spine to compensate for the frictional losses so that there is a more uniform bend radius along the length of the tapered steering spine.

The tapered steering spine can also be tailored to enhance torsional rigidity while freely flexing in a direction lateral to the longitudinal axis of the catheter. Because of the enhanced torsional rigidity, the catheter shaft can be configured to be free of torque braid in the region surrounding the tapered steering spine, thus eliminating the risk of instrumentation wires and power leads shorting against the braiding in this region and reducing the profile of the catheter generally. In one embodiment, the tapered steering spine is of a "limited bend design" to prevent excessive local bending that can be detrimental to fiber optic operation and can also cause over straining of the insulation surrounding instrumentation and power leads. Another characteristic of the tapered steering spine arrangement is that significant torsional rigidity can be provided across the entire range of deflection of the tapered steering spine. Such torsional rigidity is not limited, for example, to a fully flexed state. Accordingly, this characteristic can prove to be very useful in procedures where the spine is only moderately flexed at times, but can benefit from torsional strength at such positions.

Structurally, various embodiments of the tapered steering spine comprise a unitary tube with a plurality of axially spaced rings thereon. The rings are defined by the formation of a plurality of slots axially along the length of the unitary tube. In certain embodiments, the tangential dimension of the slots increase along the length of the tube from proximal to distal. That is, the slots that are located nearer to the distal end have a greater tangential dimension than the slots located nearer to the proximal end. In one embodiment, a straight spine portion runs along one side of the steering spine. The rings include structures on the side opposite the spine portion that engage with adjacent rings to limit the minimum bend radius when the slotted tube is bent.

In one embodiment, the axially spaced rings also include structures that engage with complimentary structures of adjacent rings. The structures and complimentary structures are tangentially centered about an axis that is diametrically opposed to the spine portion. Further, the structures and complimentary structures can be configured to engage to limit the minimum bend radius of the unitary body when the unitary body is flexed in a lateral direction away from the spine portion.

The structures can also be configured slidingly interlock to provide torsional rigidity while remaining flexible in a direction lateral to the longitudinal axis of the steering mechanism. Tip deflection is controlled with a single pull wire that is diametrically opposed to the spine portion and mechanically fastened at the distal end of the tip section without need for a soldering operation. The spine portion provides an opposing force to the deflection caused by pulling on the pull wire, thus enabling control of the curvature of the steering spine. The enhanced torquablity provided by the slidingly interlocking structures enables thinner walled materials to be utilized without sacrificing torsional strength.

A catheter shaft is also disclosed having discretely varying stiffness along the length. In one embodiment, leads are imbedded in the wall of the shaft, forming a helical shape. The helical shape enables the catheter shaft to bend without exerting undue stress on the wiring or attachment points.

One embodiment of the invention includes a deflecting tab configured on the distal end of the tapered steering spine for coupling with the pull wire. A hook shape is formed on the distal end of the pull wire and hooked to the tab. The tab can deflect radially inward when the catheter shaft is slid over the tapered steering spine, thus preventing the catheter shaft to take on an irregular shape after assembly and enabling tighter tolerance between the catheter shaft and the tapered steering spine.

In another embodiment of the invention the high-torque catheter with deflectable tip includes a steering spine defining a central axis and disposed within a catheter shaft. A plurality of cables and elongate accessories are disposed within the steering spine. The steering spine is adapted for flexing in a direction lateral to a central axis, the steering spine having a tapered construction so that flexibility of the steering spine increases from a proximal end to a distal end. The flexibility is tailored to compensate for friction between the steering spine and the pull wire, and can also be tailored to compensate for friction between the steering spine and the plurality of cables and elongate accessories along the length of the tapered steering spine as well. The tailoring of the flexibility along the length of the steering spine can provide for a substantially uniform bend radius of the tapered steering spine when flexed. The steering spine also includes structures that slidingly engage in a direction parallel to the central axis to enable the flexing of the tapered steering spine in the direction lateral to the central axis while enhancing torsional rigidity of the deflectable tip. The portion of the catheter shaft region surrounding the tapered steering spine does not contain a torque braid.

In an additional embodiment, the catheter system includes an elongate catheter assembly having a proximal portion, a distal portion and a middle portion. The distal portion includes a steering section and an end effector. The proximal portion is operatively coupled with a handle to augment operation of the catheter system. The steering section has a length and includes a tapered steering spine including a unitary body comprising a plurality of axially spaced rings and a continuous straight spine portion that runs along one side of the tapered steering spine. The steering spine has varying flexibility along the length and structures which slidingly engage one another to provide torsional rigidity.

In another embodiment, the method of making a tapered steering spine for a catheter system includes providing a unitary tube of a material having a high elastic modulus and a radius of defection. The method further includes forming slots in the unitary tube defining a plurality of slots spaced axially along the length of the unitary tube and defining a plurality of axially spaced rings that slidingly engage to provide torsional rigidity. In one configuration, the sliding engagement between the axially spaced rings is continuous from a substantially straight orientation through a maximum deflection orientation. The method also includes coating the unitary tube with a high lubricity coating and fixing a catheter shaft to the unitary tube.

In yet another embodiment of the invention, the method of correcting a non-uniform bend radius in a steering spine is disclosed. The method includes providing a tapered steering spine having a gradual decrease in beam thickness along the steering spine and a local curvature radii proportional to the third power of a beam thickness reduction factor.

In another embodiment, the tapered steering spine for a catheter system includes a unitary body of generally tubular shape having a proximal end and a distal end and defining a longitudinal axis. The unitary body including a plurality of axially spaced rings that extend from a continuous spine portion and the spine portion is parallel to the longitudinal axis. In the steering spine, the plurality of axially spaced rings define a plurality of slots along the length of the unitary body and each slot has a tangential dimension on the surface of the unitary body. The tangential dimension of the respective slots increase from the proximal end to the distal end of the unitary body to provide increasing flexibility of the unitary body from the proximal end to the distal end. The axially spaced rings each include a tongue portion and a groove portion, each being tangentially centered about an axis that is parallel to the longitudinal axis and in diametric opposition to the spine portion. Also, the tongue portion of each ring includes an axial projection extending from a pair of tongue shoulder portions, the axial projection having a tangential width and an axial length. The tongue portion has a tangential tongue width and an axial tongue length. The groove portion of each ring is defined by a pair of groove shoulder portions tangentially spaced apart to define an axial groove having a tangential width and an axial length. In one embodiment, the axial length of the groove can be greater than the axial length of the axial projection so that the tongue shoulder portions and the groove shoulder portions engage when the unitary body is in the maximum deflection orientation to limit the bend radius. The tapered steering spine can further include a single pull wire fastened at the distal end of the unitary body that is diametrically opposed to the spine portion to control tip deflection.

BRIEF DESCRIPTION OF THE DRAWINGS

FIG. 2 is a perspective view of a tapered steering spine in an embodiment of the invention;

FIG. 2A is a perspective view of a tapered steering spine with laterally flexible regions in an embodiment of the invention;

FIG. 3 is an enlarged partial view of the tapered steering spine of FIG. 2;

FIG. 3B is an enlarged partial view of the tapered steering spine in an embodiment of the invention;

FIG. 3C is an enlarged partial view of the tapered steering spine of FIG. 3B;

FIG. 3D is an enlarged partial view of the tapered steering spine of FIG. 3B;

DETAILED DESCRIPTION

Figure 1:
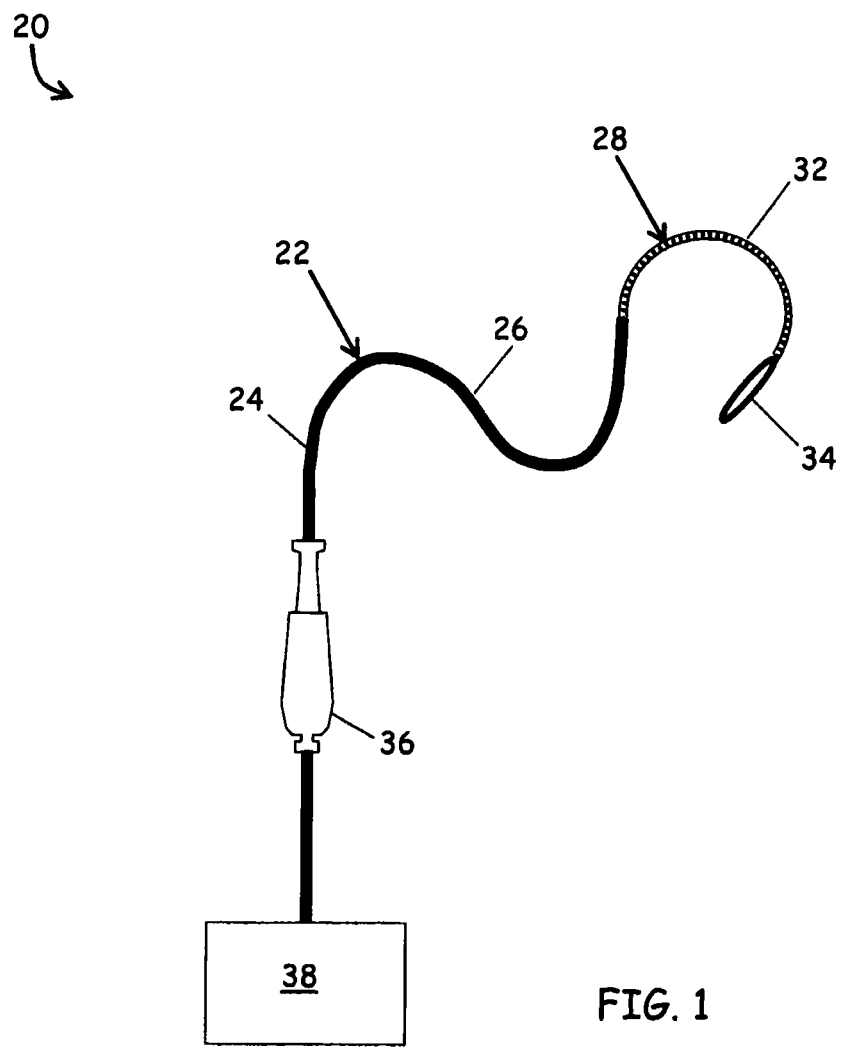
FIG. 1 is a schematic representation of a catheter system in an embodiment of the invention.

Referring to FIG. 1, a catheter system 20 is depicted in an embodiment of the invention. The catheter system 20 comprises an elongate catheter assembly 22 having a proximal portion 24, a middle portion 26 and a distal portion 28. The distal portion 28 includes a steering section 32 and an end effector 34. The catheter assembly 22 can include elongate internal components that extend through the proximal, middle and distal portions 22, 24 and 26, such as fiber optics, power leads, instrumentation leads, a pull wire and an irrigation lumen. In one embodiment, the proximal portion is operatively coupled with a handle 36. The handle 36 may be operatively coupled with various appurtenances 38 to augment the operation of the catheter system 20. Non-limiting examples of appurtenances 38 include power sources and/or irrigation systems for sourcing the end effector 34, electromagnetic sources for sourcing fiber optic systems within the catheter system 20, data acquisition devices for monitoring instrumentation of the catheter system 20, and/or control systems for controlling the sourcing of the end effector 34. A "unitary body", for purposes of this application, is a body that, in its final form, is a continuous single piece member.

Referring to FIGS. 2 through 12, a tapered steering spine 40 is depicted in an embodiment of the invention that can be utilized as the steering section 32 of the distal portion 28 of the elongate catheter assembly 22. Herein, a "steering spine" is a steering mechanism that is formed from a unitary body, such as a tube or wire, with the unitary body being slotted or grooved in a way that defines a continuous portion that extends throughout the length of the steering mechanism. Moreover, a "tapered steering spine" is a steering spine that has increasing flexibility from a proximal portion to a distal portion. This shape and flexibility permits the steering spine to be controlled in straight configurations as seen in FIG. 2 as well as in an infinite number of deflected configurations similar to the one depicted in FIG. 5, for example.

The tapered steering spine 40 comprises a plurality of slots 42 that are formed along a longitudinal axis 44 of a unitary body 46. The plurality of slots 42 define a series of axially spaced rings 48 that are integral with a straight spine portion 50 that runs along one side of the tapered steering spine 40. In one embodiment, the each slot 42 defines a pair of lateral openings 52a and 52b and a tongue-and-groove structure 53 that includes a tongue portion 54 and a groove portion 56. The tongue portion 54 can be characterized as having a tangential or lateral width 58 and an axial length 60 that extends from a pair of shoulder portions 62a and 62b. The groove portion 56 can be characterized has having an axial depth 66, a lateral width 68 and as defining a pair of shoulder portions 70a and 70b. In one embodiment, the axial depth 66 of the groove portion 56 is of greater dimension than the axial length 60 of the tongue portion 54.

A pull wire 72 extends into the tapered steering spine 40. The pull wire 72 is connected to the distal end of the tapered steering spine 40 and is radially offset so that it is diametrically opposed to the straight spine portion 50.

Each of the plurality of slots can be characterized as having a tangential dimension 78. Herein, a "tangential dimension" is an arc length at the outer diameter of the unitary body 46 at a fixed axial location. Accordingly, the tangential dimension 78 appears as a lateral dimension in the unrolled views of FIGS. 7A through 10.

Figure 9:
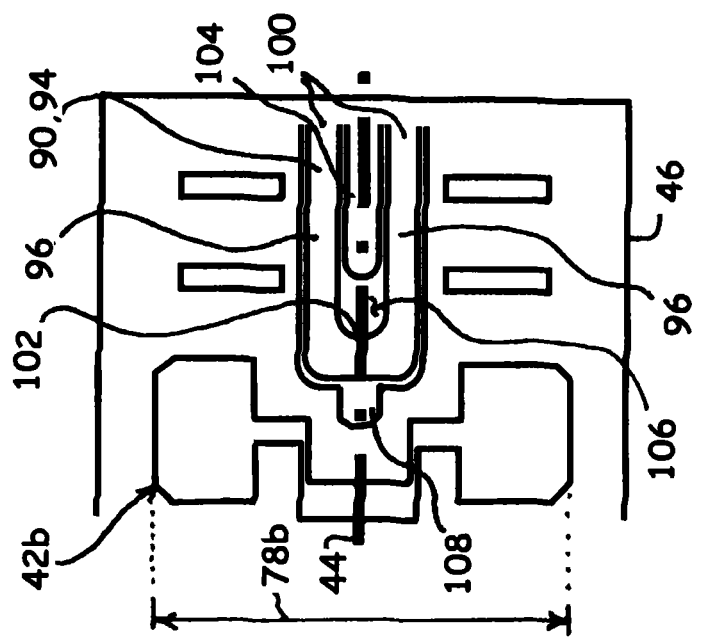
FIG. 9 is an enlarged unrolled plan view of the distal-most slot and a deflecting tab structure of FIG. 7A.
Figure 8:
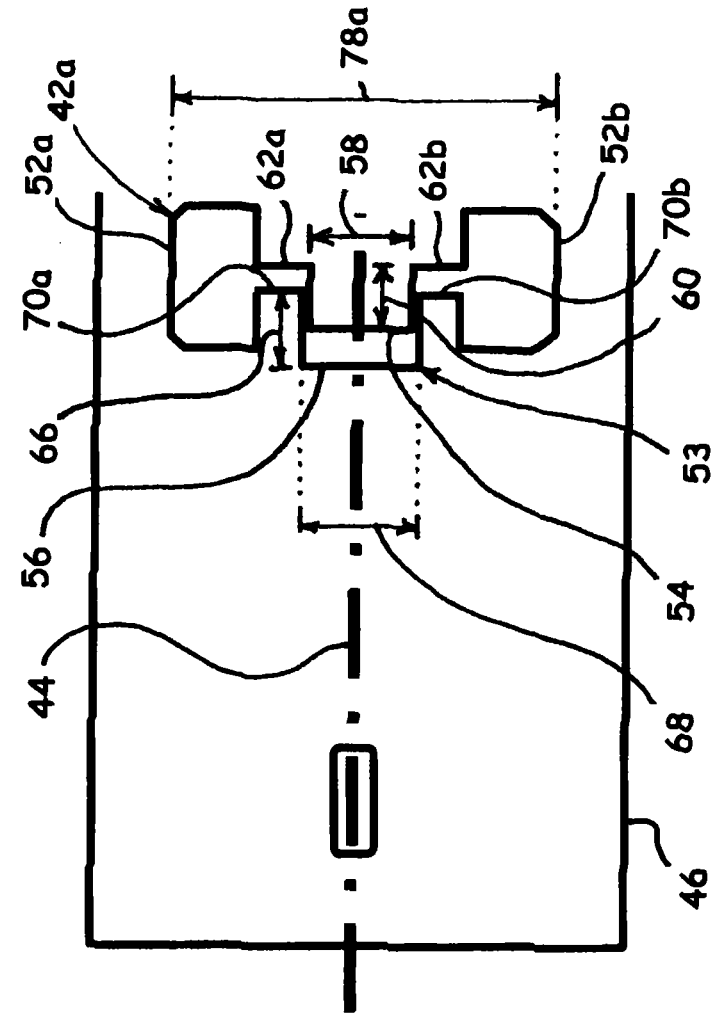
FIG. 8 is an enlarged unrolled plan view of the proximal-most slot of FIG. 7A.
Figure 10:
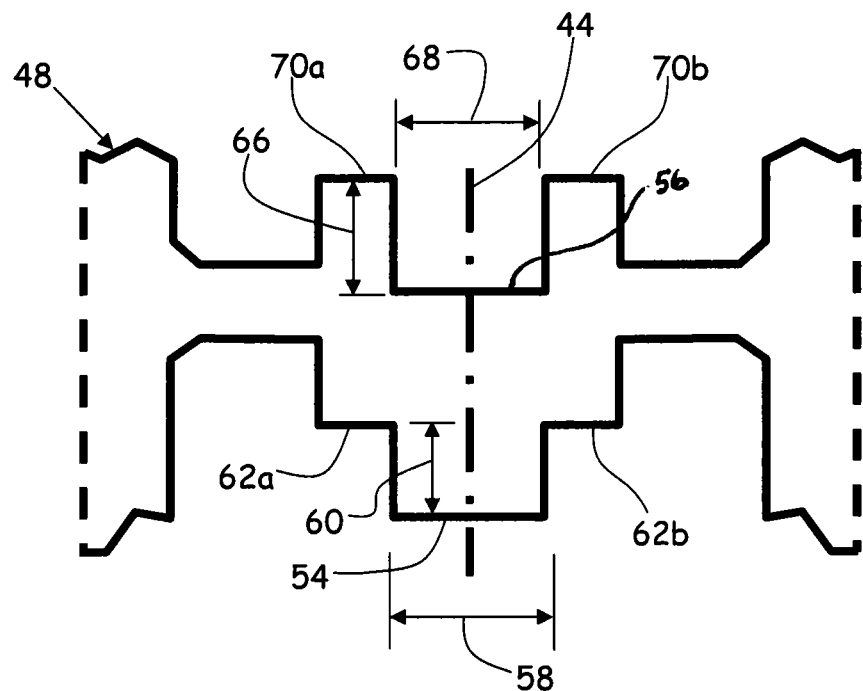
FIG. 10 is an enlarged, isolated unrolled plan view of a ring of FIG. 7A.

In one embodiment, the tangential dimensions 78 of the slots progressively increase from the proximal to the distal end of the tapered steering spine 40, as depicted in FIGS. 6 through 10. In this embodiment, a proximal end slot 42a has a tangential dimension 78a (FIG. 8) that is less than a tangential dimension 78b of a distal end slot 42b (FIG. 9). In the depicted embodiment, the tangential dimensions 78 of the plurality of slots 42 between slots 42a and 42b increase monotonically (linearly) along the length of the tapered steering spine 40 from proximal to distal. For linearly increasing tangential dimensions 78 of the plurality of slots 42 from proximal to distal, a divergence angle 80 is defined. In the depicted embodiment, the divergence angle 80 is on the order of 0.1°, which is provided as an example only and is not to be construed as limiting.

Figure 7A:
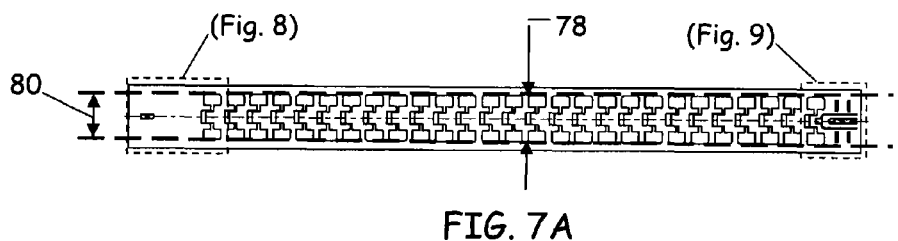
FIG. 7A is an unrolled plan view of the tapered steering spine of FIG. 2 where the spine has been split along the axis of the spine for illustrative purposes.
Figure 7B:
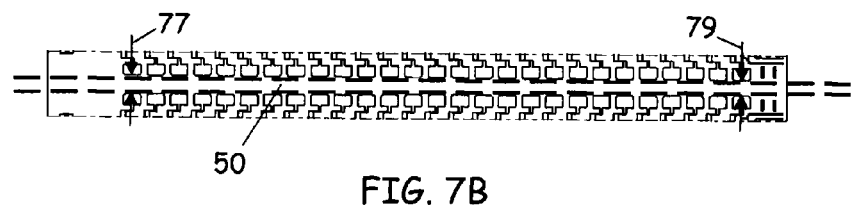
FIG. 7B is an unrolled plan view of the tapered steering spine of FIG. 2 where the spine has been split along the tongue portion of the spine for illustrative purposes.

Similarly, FIG. 7B depicts an unrolled plan view of a tapered steering spine which has been split along a longitudinal axis passing through the tongue and groove portions 54 and 56 of the tapered steering spine (rather than along the continuous straight portion 50 of the spine as depicted in FIG. 7A). The narrowing of the width of the spine from the proximal end to the distal end is depicted in FIG. 7B. For example, the width of the straight, continuous portion 50 of the spine at the proximal-most slot 77 can be seen to be slightly wider than at the distal-most slot 79.

Figures 4A, 6:
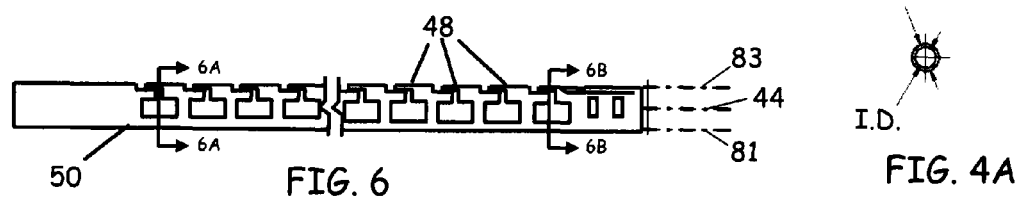
FIG. 4A is an end view of the tapered steering spine of FIG. 4.
FIG. 6 is a side view of the tapered steering spine of FIG. 4.
Figure 6A:
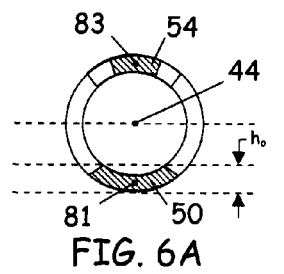
FIG. 6A is a cross-sectional view of the tapered steering spine of FIG. 6 along line 6A-6A.
Figure 6B:
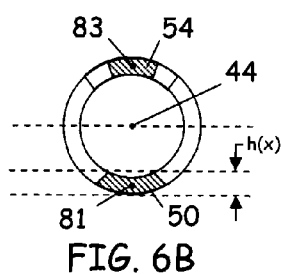
FIG. 6B is a cross-sectional view of the tapered steering spine of FIG. 6 along line 6B-6B.

The increased size of the slots 42 can also be better understood from FIGS. 6, 6A and 6B. A side view of the tapered steering spine is presented in FIG. 6, in which a first axis 81 runs through the continuous spine portion 50 such that it is generally parallel to the central longitudinal axis 44 of the spine when in an unflexed state. Further, a second axis 83 is centrally located relative to the tongue and groove structures 53 in a location diametrically opposed to the spine portion 50 and its axis 81. Based on this arrangement, cross sections are taken of the steering spine 40 at a first location in the proximal-most slot (FIG. 6A) and at a second location in the distal-most slot (FIG. 6B). Note that the spine portion 50 in FIG. 6A is larger than the spine portion 50 of FIG. 6B due to the increased slot sizes in FIG. 6B. The significance of the resulting change in beam thickness is discussed later in greater detail below.

Referring again to FIG. 10, an unrolled plan view of one of the plurality of axially spaced rings 48 that define the slots 42 along the length of the tapered steering spine 40 is depicted. The axial spacing between the rings 48 can be uniform, as depicted in the figures. Optionally, the axial spacing can be varied along the axis as another way to provide variable stiffness along the length of the tapered steering spine 40.

Various embodiments of the tapered steering spine 40 can include a deflecting tab structure 90 for coupling the pull wire 72 (FIG. 3). In one embodiment, the deflecting tab structure 90 can be of a U-shape 94 having legs 96 that are cantilevered from the distal end of the unitary body 46. The U-shape 94 defines an inside length 98 of the legs 96, measured between an anchor datum 100 of the legs and an interior apex 102 of the U-shape 94. A stop portion 104 can also be extended from the distal end of the unitary body 46 between the legs 96 and defining a gap 106 between the proximal end of the stop portion 104 and the apex 102 of the U-shape 94. The tapered steering spine 40 can also be configured to define a passage 108 through the wall of the unitary body 46 that borders the proximal end of the U-shape 94. In one embodiment, the pull wire 72 is configured to define a hook portion 110 at the distal end for coupling to the deflecting tab structure 90.

Referring again to FIG. 2A, the elongated catheter assembly 22 can comprise a plurality of laterally flexible regions 136 positioned along the length of the elongated catheter assembly 22. The plurality of laterally flexible regions 136 can be positioned in areas that benefit from additional flexibility as the elongated catheter assembly 22 is navigated through the biological lumen.

Figure 3A:
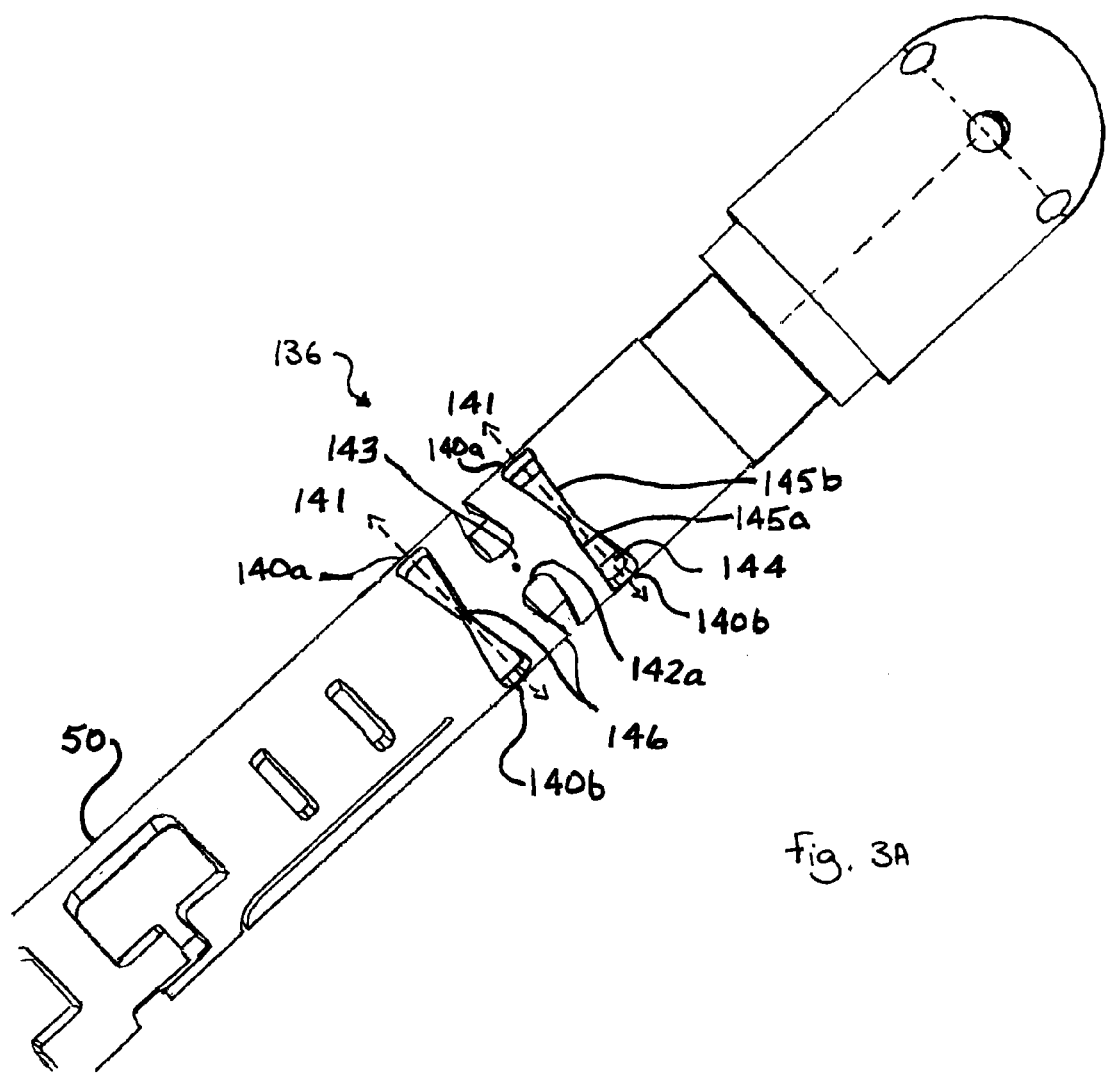
FIG. 3A is an enlarged partial view of the tapered steering spine of FIG. 2A.
Figure 4:
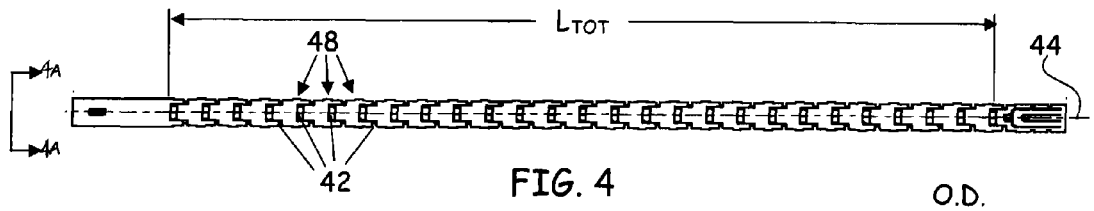
FIG. 4 is a plan view of the tapered steering spine of FIG. 2.

Referring to FIG. 3A, an example laterally flexible region 136 is depicted in an embodiment of the invention having at least one pair of flexures 140*a* and 140*b* that are in diametric opposition to each other. In the depicted embodiment, the flexure 140*a* is in line with the spine portion 50. A perpendicular axis 141 is defined that passes through both flexures 140*a* and 140*b* and is perpendicular to the longitudinal axis 44 of the tapered steering spine 40. The flexures 140*a* and 140*b* provide axial stiffness to the tapered steering spine 40. The laterally flexible region 136 can also define one or more slits 144, each having a proximal side 145*a* and a distal side 145*b* and ends defined by the respective flexures 140*a* or 140*b*.

The flexible region 136 can also include offset flexures 142*a* and 142*b* (flexure 142*b* being hidden from view in FIG. 3A). The offset flexures 142*a* and 142*b* are also in diametric opposition to each other and are rotationally offset from the flexures 140*a* and 140*b*. In the depicted embodiments of FIGS. 2A and 3A, the offset flexures 142*a* and 142*b* are rotationally offset 90° from the flexures 140*a* and 140*b* to define an offset axis 143 that is substantially orthogonal to both the perpendicular axis 141 and the longitudinal axis 44 of the tapered steering spine 40.

In one embodiment of the invention, a plurality of such flexure pairs 140*a*, 140*b* are oriented to define a plurality of perpendicular axes 141, the perpendicular axes 141 being parallel to the steering plane. (The "steering plane" is defined as the plane in which the tapered steering spine 40 flexes when pulled by the pull wire 72.) In some embodiments, there are at least two flexure pairs 140*a*, 140*b* for every offset flexure pair 142*a*, 142*b*. At least one projection 146 can also be formed by the shape of the slit 144 to reduce the effective width of the slit 144.

Functionally, the laterally flexible regions 136 (FIGS. 2A and 3A) are configured generally to provide flexibility in directions lateral to the spine portion 50. The flexures 140*a* and 140*b* act as hinges about which the tapered steering spine 40 can flex. Multiple flexure pairs can provide multiple points about which the tapered steering spine 40 can flex in a single plane. Inclusion of offset flexure pairs 142*a*, 142*b* in combination with the flexure pairs 140*a*, 140*b* enable flexing of the tapered steering spine 40 in multiple directions and planes.

In operation, flexing the tapered steering spine 40 about the perpendicular axis 141 and/or the offset axis 143 causes at least one of the slits 144 to decrease in width. If the flexing force is great enough, the proximal and distal sides 145*a* and 145*b* of a given slit 144 will contact each other, thus restricting further flexing of the tapered steering spine 40 in that direction. The projection(s) 146, when implemented, serve to limit the extent to which the tapered steering spine 40 rotates about the axes 141, 143 thereby limiting the extent to which the tapered steering spine 40 can laterally flex. This arrangement enables the paired flexures 140*a*, 140*b* and/or 142*a*, 142*b* to be of a longer axial length for enhanced flexibility while limiting the rotational displacement of the laterally flexible region 136 to prevent hyperextension of the paired flexures 140*a*, 140*b* and/or 142*a*, 142*b*.

Referring to FIGS. 3B-3D, a laterally flexible region 137 tailored to accommodate the deflection tab structure 90 is depicted in an embodiment of the invention. An unpaired flexure 148 acts as a hinge that enables the tapered steering spine 40 to flex about an axis 150 substantially perpendicular to the longitudinal axis 44 of the tapered steering spine 40 while providing axial stiffness to the tapered steering spine 40. The unpaired flexure 148 can be wider than the counterpart paired flexures 140 to mitigate against fatigue fracture caused by repeated flexing. In the depicted embodiment, the laterally flexible region 137 further comprises slits 152 that are positioned on either side of the unpaired flexure 148 configured to limit the extent to which the tapered steering spine 40 can rotate about the perpendicular axis 150. Each slit 152 includes a proximal side 153*a* and a distal side 153*b* and is adapted to intersect the passage 108 extending at least partly around the U-shape 94.

Functionally, the laterally flexible region 137 (FIGS. 3B-3D) provides flexibility lateral to the spine portion 50 akin to the laterally flexible region(s) 136, but is configured to accommodate the deflecting tab structure 90. In operation, flexing the tapered steering spine 40 about the perpendicular axis 150 in a first direction causes one of the slits 152 to decrease in width until the proximal and distal sides 153*a* and 153*b* contact each other, thereby restricting further flexing of the tapered steering spine 40 in that direction (FIG. 3D). The passage 108 can be shaped such that the U-shape 94 is in constant contact with the wall of the unitary body 46 regardless of the angle of deflection about axis 150. The contact between the tip of the U-shape 94 and the passage 108 provides axial stiffness under compression and serves to counterbalance the action of the unpaired flexure 148, thereby restricting bending of the laterally flexible region 137 substantially about the perpendicular axis 150. That is, the counterbalancing effect of the contact between U-shape 94 and passage 108 militates against spurious rotation about axes other than perpendicular axis 150.

According to an embodiment of the invention, the laterally flexible regions 137 can comprise at least one projection 154 to reduce the effective width of the deflection tab slit 152, thereby limiting the extent to which the tapered steering spine 40 rotates about the perpendicular axis 150. This arrangement enables the unpaired flexure 148 a longer axial length for enhanced flexibility while limiting the rotational displacement of the laterally flexible region 137.

The tapered steering spine 40 may be constructed of any material that provides the necessary radius of deflection without yielding and has a high elastic modulus. Example materials include nickel-titanium alloys (e.g., NITINOL), nickel-cobalt alloys (e.g., NIVAFLEX) and spring steel. The slots 42 can be cut using techniques known in the industry such as laser cutting and electroerosion wire cutting. The tapered steering spine 40 can be coated with a high lubricity coating such as polytetrafluoroethylene (PTFE), fluorinated ethylene propylene (FEP) and poly(p-xylylene) polymers (PARYLENE). In one embodiment, the coating does not extend over a few millimeters near the proximal and distal ends of the tapered steering spine 40 to provide bonding surfaces for affixing the catheter shaft to the tapered steering spine 40 (discussed below).

Figure 16:
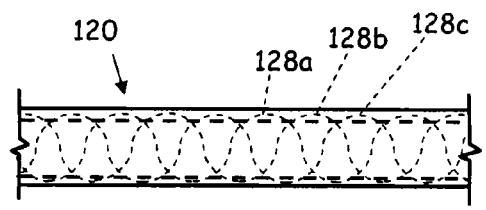
FIG. 16 is a schematic view of a section of the catheter shaft depicting embedded lead wires arranged in a helical shape.

Referring to FIGS. 13 through 16, a catheter shaft 120 is depicted in an embodiment of the invention. The catheter shaft 120, which defines a longitudinal axis 121 and also defines the outer periphery of the elongate catheter assembly 22, comprises a flexible tube 122 and a trio of electrodes 124*a*, 124*b* and 124*c* (referred to collectively as the electrodes 124) at a distal portion 126 of the catheter shaft 120. Each electrode 124*a*, 124*b* and 124*c* is connected to a respective lead wire 128*a*, 128*b* and 128*c* (referred to collectively as the lead wires 128). In one embodiment, the lead wires 128 are insulated and are imbedded in the wall of the catheter shaft 120, each defining a helical shape within the catheter shaft 120, as depicted in FIG. 16 for example. This type of helical arrangement enables the lead wires 128 to flex when the catheter system flexes without creating unwanted resistance to the flexing and without putting undue strain on the lead wires 128.

In one embodiment, the lead wires 128 comprise a single conductor coated with an electrically insulating enamel coating. In another embodiment, the lead wires 128 can each further comprise a plurality of wire strands braided together to form the lead wire 128 and can also be coated with an electrically insulating enamel coating. Each wire strand can be individually enameled before the wire strands are braided together. Alternatively, the wire strands of the lead wires 128 can be braided together to form the lead wires 128 before being enameled together.

In one embodiment, the catheter shaft 120 comprises an inner liner 130 and an outer layer 132, with the lead wires 128 being located at the interface therebetween or imbedded in the outer layer 132. Optionally, a torque braid 134 can also be disposed at the interface and is in intimate contact with the insulation of the lead wires 128. The torque braid 134 can also be comprised of enameled braid wire, providing an additional barrier against the development of a short between the torque braid 134 and the lead wires 128. In one embodiment, wires comprising the torque braid are provided with an enamel coating prior to formation of the torque braid 134. Alternatively or in addition, the enamel coating is applied to the torque braid 134 after braiding. The enamel coating for the wires (lead wires 128 or the braid wires for the torque braid 134) can comprise, for example, polyimide, polyimide-amide, polyurethane, NYLON or PTFE.

The inner liner 130 and outer layer 132 can be comprised of a PEBAX grade polymer. Representative and non-limiting dimensions for the cross-section of the catheter shaft 120 is a thickness of 0.06 mm for the inner liner 130 and a thickness of 0.2 mm for the outer layer 132, providing an inner diameter of approximately 1.8 mm and an outer diameter of approximately 2.3 mm (i.e. 7 French).

The torque braid 134 may comprise flat wire braiding (e.g., 0.001 inch by 0.003 inch wire cross section) or round wire braiding (e.g., 0.0015 inches double round wire) of stainless steel. The torque braid 134 can extend the entire length of the catheter shaft 120. Alternatively, the torque braid 134 can extend only along only a portion of the catheter shaft 120.

Figure 13:
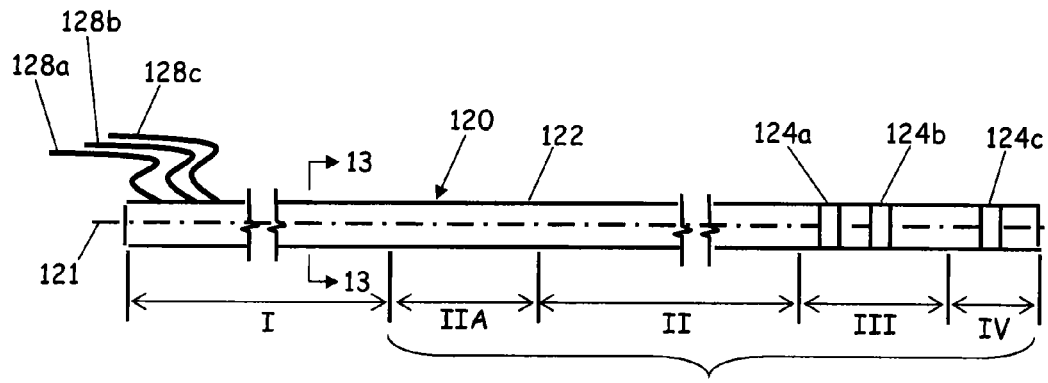
FIG. 13 is a side view of a catheter shaft in an embodiment of the invention.
Figure 14:
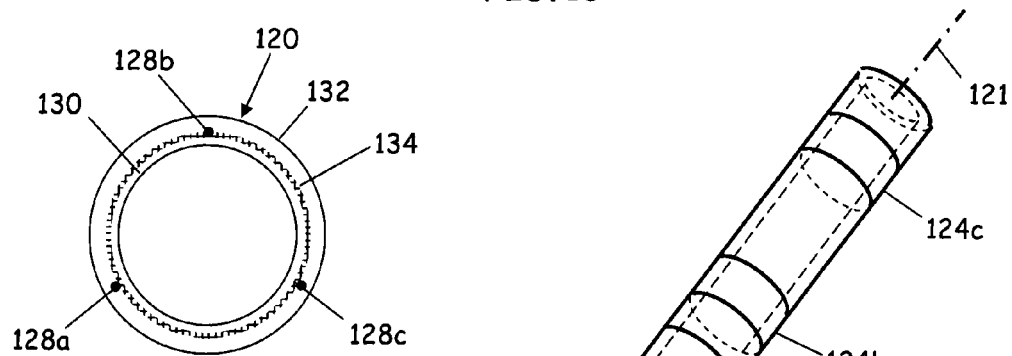
FIG. 14 is an enlarged sectional view of the catheter shaft of FIG. 13.
Figure 15:
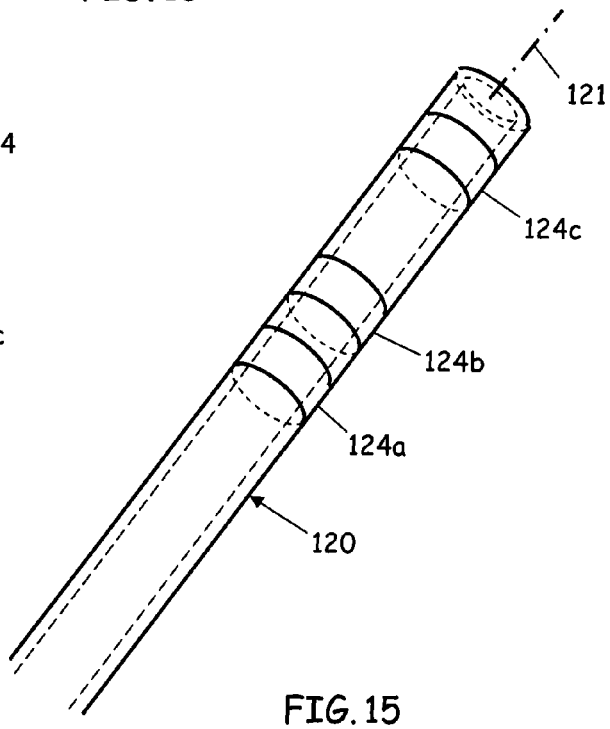
FIG. 15 is a perspective view of the distal end of the catheter shaft of FIG. 13.

In assembly, the electrical connection between electrodes 124 and the lead wires 128 can be established by a soldering process prior to embedding the lead wires 128 in the catheter shaft 120. In one embodiment, the lead wires 128 extend laterally from the wall of the catheter shaft 120 near the proximal end of the catheter shaft 120, as depicted in FIG. 13. Optionally, the lead wires 128 can extend axially out the proximal end of the catheter shaft 120 (not depicted).

The catheter shaft 120 can be designed to have sections of discretely varying stiffness. In the depicted embodiment, the catheter shaft 120 is divided into five sections I, IIA, II, III and IV. Section I comprises a majority of the length of the catheter shaft (in one embodiment about 95% of the length). Sections IIA, II, III and IV are all located in the distal portion 28 of the elongate catheter assembly 22. Representative and non-limiting lengths of the various sections are: Section I=1164 mm; Section IIA=8 mm; Section II=41 mm; Section III=7 mm; and Section IV=4 mm.

The sections each have tailored stiffness characteristics as follows (stiffness expressed as durometer hardness): Section I=72D; Section IIA=55D; Section II=35D; Section III=55D; and Section IV=35D. It is understood that the preceding numbers are offered by example only and are in no way to be construed as a limiting aspect of the invention.

Functionally, the helical shape of the lead wires 128 enable the catheter shaft 120 to flex in a direction lateral to the longitudinal axis 121 without putting undue strain on the lead wires 128. Section I provides sufficient stiffness for torquing and pushing the elongate catheter body 22 through biological lumens such as veins and arteries. Section IIA provides a transitional stiffness between the stiffer section I and the plyable section II. Section II surrounds a majority of the steering section 32 and is therefore preferably plyable to conform to the flexing of the steering section 32. Section III surrounds the transition between the steering section 32 and the end effector 34, and must be relatively stiff to enable axial and lateral forces to be applied to the catheter shaft 120 without kinking. The softness of section IV is in consideration of a specific embodiment that employs a force sensor (not depicted) at the distal extremity to limit the force that is shunted by the surrounding material of the catheter shaft 120, thereby enhancing the sensitivity of the force sensor.

Because of the enhanced torque characteristics provided by the tongue-and-groove structures 53 of the tapered steering spine 40, the torque braid 134 can be excluded from the portion of the catheter shaft that surrounds the tapered steering spine 40 (corresponding roughly with sections IIA, II, III and IV). An advantage of eliminating the torque braid 134 from this portion of the catheter shaft 120 is that the risk of the torque braid 134 wearing through the insulation of the lead wires 128 and causing a short is eliminated where it is most likely to occur, i.e. in the region of the elongate catheter body 22 that experiences the greatest degree of deflection.

In assembly, the proximal end of the pull wire 72 can be inserted into the gap 106 and routed through the tapered steering spine 40 until the hook portion 110 catches the apex 102 of the U-shape 94. The hook portion 110 may tend to be proud (i.e. protrude radially) relative to the outer diameter of the tapered steering spine 40. The catheter shaft 120 can be slid over the tapered steering spine 40 and over the hook portion 110. For embodiments where the proximal and distal end portions of the tapered steering spine 40 are not coated, the catheter shaft 120 can be bonded to the tapered steering spine 40 at these locations.

Functionally, the deflecting tab structure 90 can be dimensioned to readily deflect inward (i.e. toward the longitudinal axis 44 of the tapered steering spine 40) so that the radial reaction force exerted on the catheter shaft is negligible after assembly. Herein, a "negligible" radial reaction force is one that does not deform or cause noticeable local bulging of the catheter shaft in the vicinity of the hook portion 110, thus enabling the tolerance between the catheter shaft and the tapered steering spine to the specified without the need for additional clearance that would otherwise be required to accommodate the presence of the hook. For example, during development of the invention, it was found that a tapered steering spine 40 constructed of NITINOL and having a nominal inner diameter of 1.28 mm and a nominal outer diameter of 1.65 mm will not exert a deforming force on the catheter shaft if the length 98 of the legs 96 is approximately 2 mm or greater. The material and dimensions provided in this example are illustrative only and are not to be construed as limiting. The compliance of the tab and attendant depression of the hook portion also enables a tighter tolerance fit between the tapered steering spine 40 and the catheter shaft 120.

The use of the hook portion 110 for distal attachment of the pull wire 72 negates the need for a thermal processing step, such as soldering, welding, or providing the pull wire 72 with a wider body at the distal end, such as a ball. Such a thermal-processing of the distal end of the pull wire 72 typically causes an local annealing of the pull wire material, resulting in a decrease of the yield strength of the pull wire 72 in the annealed region, initially obtained through strain hardening of the pull wire 72. The loss of yield strength of the pull wire 72 can compromise the ability to transmit the tension forces required to achieve maximum tip deflection.

The stop portion 104 prevents the hook portion 110 from sliding off the U-shape 94 when tension is released from the pull wire 72. The passage 108 enables the hook portion to have a length that extends beyond the U-shape 94 without hanging up on the unitary body 46 when the deflecting tab structure 90 is deflected radially inward.

The high lubricity coating reduces the influence of the catheter shaft 120 on the bending shape of the tapered steering spine 40 by reducing friction losses and enabling relative motion (delamination) between the outer diameter of the tapered steering spine 40 and the inner diameter of the catheter shaft 120. The relative motion can be substantial during the flexing process because the tapered steering spine 40 and the catheter shaft 120 flex about different neutral planes that are offset with respect to each other. The neutral plane of the tapered steering spine 40 is substantially along the mid-thickness of the straight spine portion 50, while the neutral plane of the catheter shaft 120 deforms substantially along the longitudinal axis 121. The high lubricity coating also reduces friction between the tapered steering spine 40 and elongate internal components that may come in contact therewith when the tapered steering spine 40 is flexed, such as the pull wire 72, wiring/cabling such as fiber optics, power leads and instrumentation leads (not depicted) and irrigation lumen (not depicted).

Figure 5:
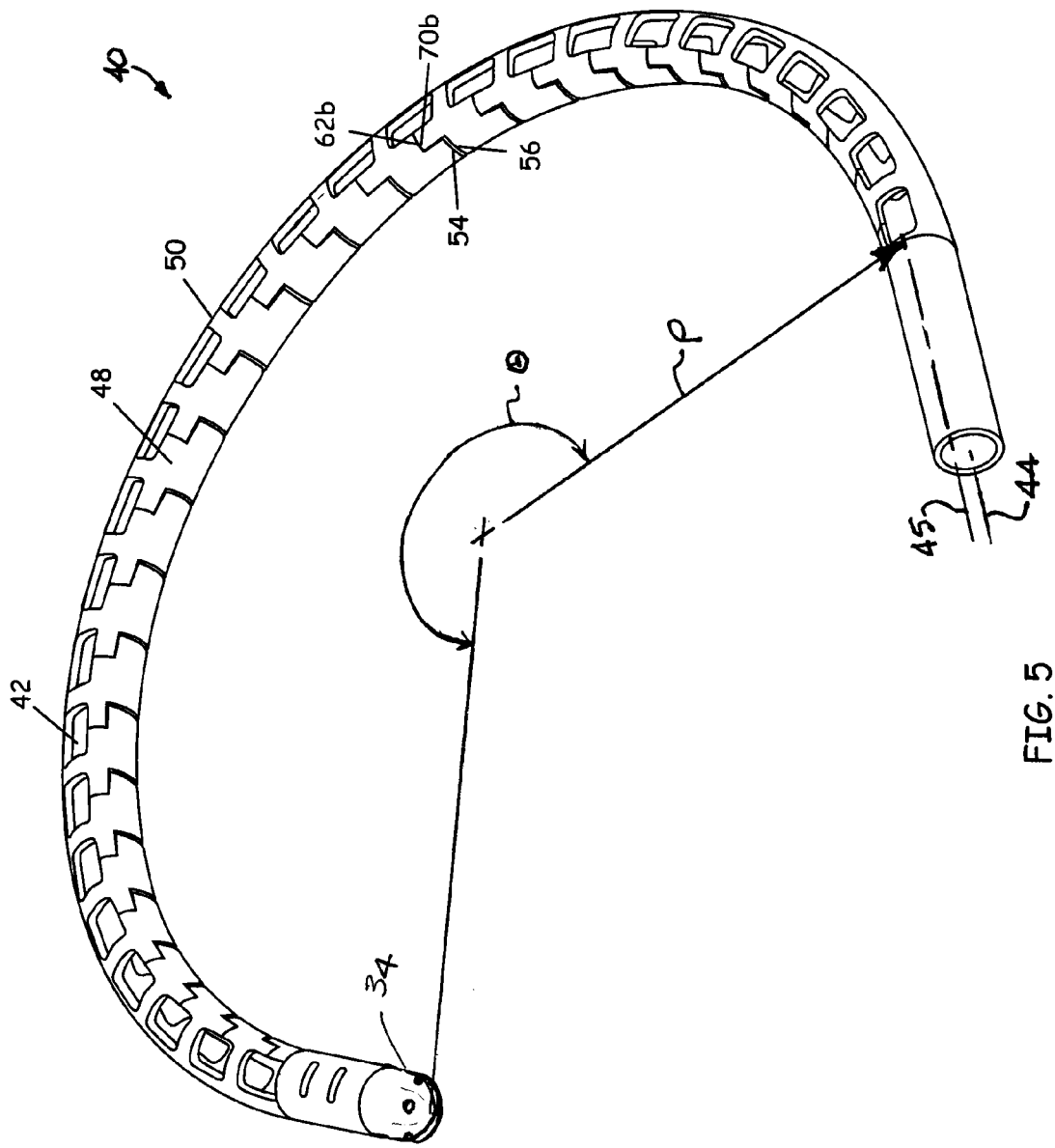
FIG. 5 is a perspective view of a tapered steering spine in a deflected position.

In operation, an operator exerts a tension force on the pull wire 72, causing the tapered steering spine 40 to deflect laterally toward the pull wire side of the tapered steering spine 40. A constant tension on the pull wire can substantially maintain the tapered steering spine 40 in a fixed deflected state. The tongue-and-groove structures 53 can be dimensioned to engage so as to limit the minimum bend radius of the tapered steering spine 40 (FIG. 5). In one embodiment, the tongue-and-groove structures 53 are dimensioned to provide a close tangential or lateral dimension therebetween such that the tapered steering spine 40 can flex freely in the lateral direction, but engage with each other when the tapered steering spine 40 is rotationally deflected about the longitudinal axis 44. In this way, the close tangential or lateral tolerance between the tongue-and-groove structures 53 enables the transmission of torque and increases the torsional rigidity of the tapered steering spine 40 over that of the straight spine portion 50 alone.

When the axial depth 66 of the groove portion 56 is of greater dimension than the axial length 60 of the tongue portion 54, the shoulder portions 62a, 62b and 70a, 70b engage when at the maximum degree of flexing. Engagement of the shoulder portions 62a, 62b and 70a, 70b provides two lines of contact that are laterally spaced apart, thus providing greater stability than if the tongue portion 54 engaged with the groove portion 56 for only a single line of contact. Engagement of the shoulder and tongue portions can be seen in FIG. 5, which depicts the tapered steering spine 40 in a deflected orientation. Engagement of the shoulder portions 62b and tongue portions can be seen as well as the spaces that remain between the tongue portions 54 and groove portions 56.

The depiction of FIG. 5 also depicts a curvature radius ρ and a deflection angle Θ of the tapered steering spine 40 in a deflected orientation. The curvature radius ρ is defined from the origin of the substantially circular arc defined by the deflected orientation of the tapered steering spine 40 to the centerline (longitudinal axis 44) of the tapered steering spine 40. (An offset axis 45, located on a plane that is offset from but parallel to the steering plane, is identified in FIG. 5 for clarity.) The deflection angle Θ is defined from the proximal end of the proximal-most ring to the tip of the end effector 34. The curvature radius ρ is a function of the deflection angle Θ, with the curvature radius ρ being inversely proportional to the deflection angle Θ.

A maximum deflection angle Θmax and a minimum curvature radius ρmin are established by the clearance between the contacting portions of the rings 48. That is, for embodiments where the shoulder portions 62a, 62b and 70a, 70b provide the lines of contact, the maximum deflection angle Θmax and the minimum curvature radius ρmin are determined by the clearance between 62a, 62b and 70a, 70b. For embodiments where the tongue and groove portions 54 and 56 are brought into contact, the maximum deflection angle Θmax and the minimum curvature radius ρmin are determined by the clearance between the tongue and groove portions 54 and 56.

In theory, a deflection angle Θ of 235° would cause the distal tip of the end effector 34 to touch the longitudinal axis 44 as projected from the proximal end of the tapered steering spine 40. As a practical matter, the maximum deflection angle Θmax is something less than 235° because of the finite thickness or diameter of the catheter assembly 22 that passes along the longitudinal axis 44. In one embodiment, the maximum deflection angle Θmax is approximately 225°. In other embodiments, the maximum deflection angle Θmax is approximately 180°. In some embodiments, the tapered steering spine 40 is designed to produce a minimum bend radius of 10 mm.

It is further noted that the tongue and groove portions 54 and 56 of the tapered steering spine 40 as depicted provides the rotational stiffness regardless of the degree of lateral bending. That is, the tongue and groove portions 54 and 56 will engage each other under rotational flexing whether the tapered steering spine 40 is in a straight orientation, at the maximum degree of flexing (minimum bend radius), or anywhere in between.

In one embodiment, the resilience of the straight spine portion 50 provides a restoring force that enables control of the bend radius and substantially restores the tapered steering spine 40 to a straight shape.

The increasing tangential dimensions 78 of the plurality of slots 42 from proximal to distal provides the variable stiffness of the tapered steering spine 40, with the stiffness decreasing from proximal to distal. The decreasing stiffness compensates for friction losses between the pull wire 72 and the tapered steering spine 40.

The friction between the pull wire and the inner diameter of the tapered steering spine 40 increasingly reduces the force transmitted by the pull wire from the proximal to the distal end of the steering device. The local bending moment $M_B(x)$ is likewise reduced, resulting in an increase of the local radius of curvature from proximal to distal. Assuming linear bending theory wherein there is a locally linear deformation for each segment, the angle of the spine deflection subjected to local bending is expected to scale linearly with the first derivative the deflection, $v'(x)$. The inverse value of the curvature radius $\rho$ is proportional to the second derivative of the spine deflection ($v''(x)$), which is linearly proportional with the bending moment of inertia Iz (Eq. 1).

$$v''(x) \sim \frac{M_B(x)}{EI_z} \sim \frac{1}{\rho} \qquad \text{Eq. (1)}$$

where E is the modulus of elasticity of the steering spine material. The bending moment of inertia Iz in turn scales with $h^3$, where h represents the beam thickness:

$$I_z \sim h^3 \qquad \text{Eq. (2)}$$

Solving for the curvature radius $\rho$ yields:

$$\rho \sim \frac{h^3}{M_B(x)} \qquad \text{Eq. (3)}$$

The beam thickness h can be a constant value, or can vary along the spine axial coordinate following a given function $h(x)$. If $M_B(x)$ decreases with x as a consequence of the pullwire friction, the local radius of curvature $\rho$ typically increases for a constant beam thickness h. Under such circumstances, $h(x)$ can be correspondingly decreased to compensate for the decreasing $M_B(x)$ and improve the uniformity of the radius of curvature $\rho$ along the structure.

An example of decreasing beam thickness can be further understood based on FIGS. 6, 6A and 6B. In FIG. 6A, $h_0$ represents the initial beam thickness of the proximal location of the continuous spine 50, while, in FIG. 6B, $h(x)$ represents beam thickness at a more distal location on the spine. The initial beam thickness $h_0$ is greater than the beam thickness $h(x)$ because of the tangential dimension of the continuous spine 50 is greater at the proximal end than at the more distal location of $h(x)$.

Under these assumptions, a suitably chosen gradual decrease of the beam thickness $h(x)$ in the distal direction, providing local curvature radii proportional to the third power of the beam thickness reduction factor (Eq. (3)). In theory, the formulations can be used to compensate for the pull wire frictional loss to achieve a more uniform bend radius along the length of the tapered steering spine 40.

Figure 12:
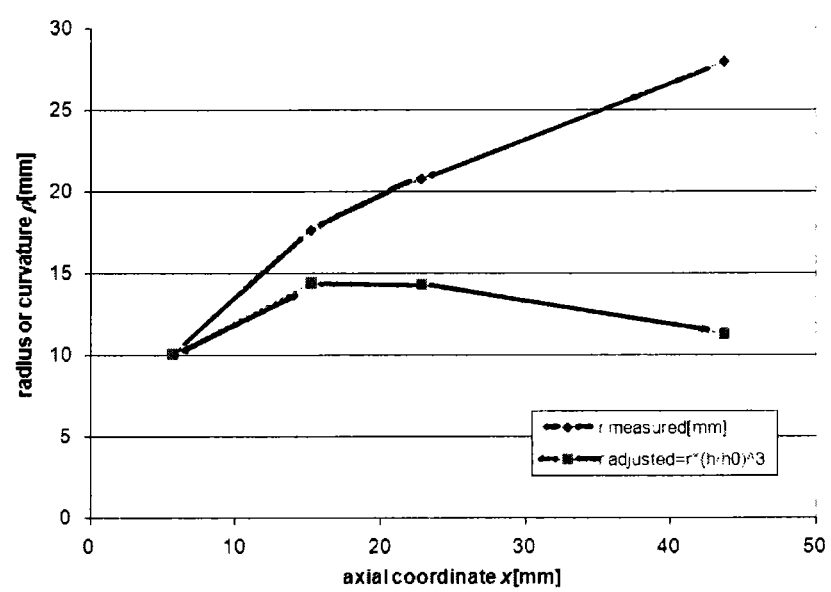
FIG. 12 is a graph of the measured local radii of the non-tapered steering spine of FIG. 11 and the theoretical adjusted local radii of the tapered steering spine in an embodiment of the invention.
Figure 11:
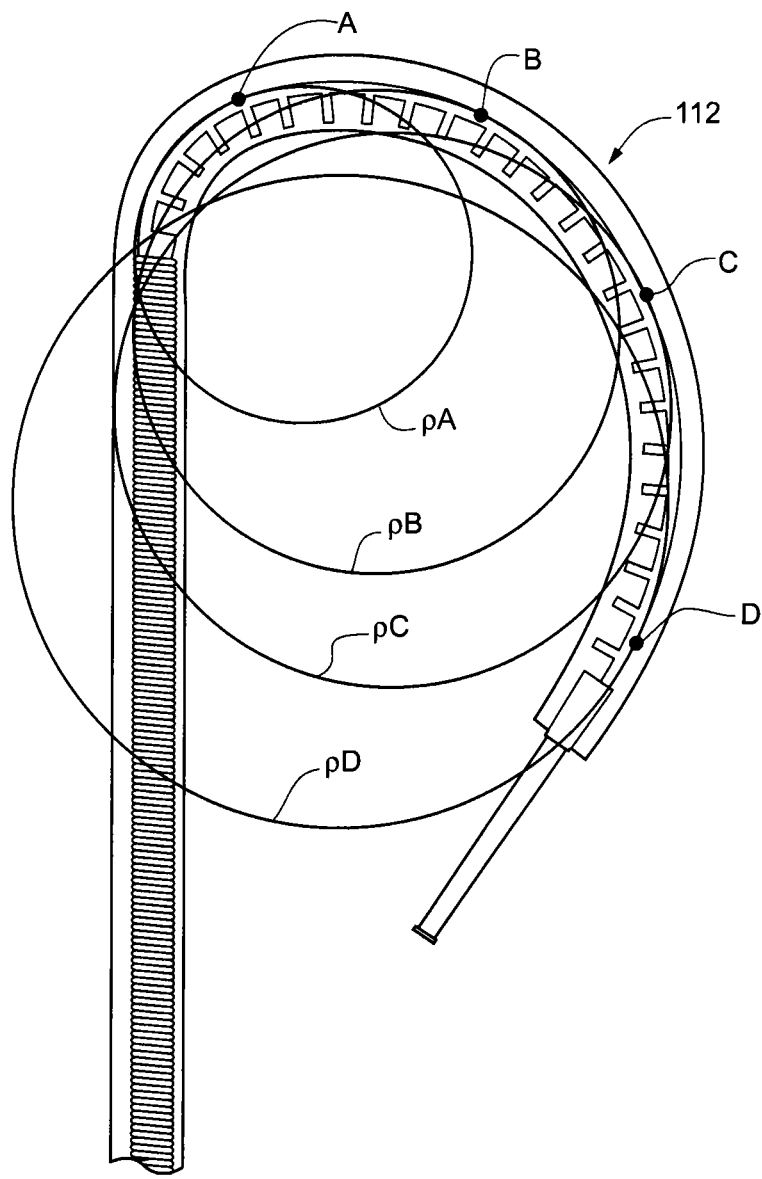
FIG. 11 is a side view of a non-tapered steering spine.

Referring to FIGS. 11 and 12, the bending shape of a non-tapered spine 112 having a flexible beam of constant thickness (and therefore the same as the proximal thickness $h_0$) was evaluated under pull wire tension to establish the effect of friction losses. A tension force was applied to the pull wire, causing the non-tapered spine to flex. The local radii of curvature $\rho$ were then measured at different axial locations A, B, C and D, each located at a unique axial distance x referenced from the proximal end of the non-tapered steering spine 112. The local radii of curvature $\rho$ corresponding to locations A, B, C and D are designated $\rho A$, $\rho B$, $\rho C$ and $\rho D$, respectively, in FIG. 11. The results are tabulated in Table 1 and graphed in FIG. 12. Results indicate an increasing radius of curvature towards the distal end (high x values), as a consequence of the frictional losses to force exerted by the pull wire force loss.

Applying the theoretical formulations of Eqs. (1) through (3), the influence of a linear beam thickness $h(x)$ tapering follows the relationship $$h(x) = h_0 - (\Delta h/L)x \qquad \text{Eq. (4)}$$

where $0 < x < L$, $\Delta h$ is the change in beam thickness over a representative length L of the portion to be tapered. Because the bending radius of a beam is believed to be substantially proportional the beam thickness cubed ($h^3$, Eq. (2)), a local curvature radius correction factor is derived:

$$(h(x)/h_0)^3 \qquad \text{Eq. (5)}$$

where $h(x)$ is given in Eq. (4) and the constant beam thickness $h_0$ is the maximum beam thickness at the proximal end of the tapered beam portion.

For this example, $h_0 = 0.35$ mm, $L = 50$ mm and $\Delta h$ was established at 0.12 mm to provide a more uniform local bending radius $\rho$ as per Eq. (3). A resulting adjusted radius parameter $\rho$adjusted is given in Table 1 and graphed in FIG. 12. The subsequent angle of divergence is given by $$\tan^{-1}(\Delta h/L) = \tan^{-1}(0.12/50) = 0.14° \qquad \text{Eq. (6)}$$

TABLE 1

| Location | x [mm] | $\rho(x)$ [mm] | $\rho_{adjusted}$ [mm] = $\rho(x)[h(x)/h_0]^3$ where $h(x) = h_0 - (\Delta h/L_{tot})x$ |
|---|---|---|---|
| A | 5.7 | 10.0 | 10 |
| B | 15.2 | 17.6 | 14.4 |
| C | 22.8 | 20.8 | 14.3 |
| D | 43.7 | 27.9 | 11.2 |

The preceding is based on a beam thickness that decreases linearly along the tapered steering spine 40. A non-linear beam thickness dependency can also be utilized to improve on the uniformity of the local radii of curvature. Other effects on the bending radii, such as the catheter shaft and friction between the spine and shaft, can also be added to the experimental set up, but using substantially the same technique. The curve fit parameter (e.g., $\Delta h$ in the example above) can be determined iteratively or by least-squares line fitting techniques.

Accordingly, a method for determining the tapering of a steering spine is as follows:
providing an non-tapered steering spine having a proximal end and a distal end and defining a longitudinal axis, the non-tapered steering spine including a plurality of axially spaced rings that define a plurality of slots therebetween, each of the rings being substantially identical and each of the slots being substantially identical, the non-tapered steering spine having a constant beam thickness $h_0$ and having a total axial length $L_{TOT}$ defined between the proximal boundary of a proximal-most of the plurality of slots and a distal boundary of a distal-most of the plurality of slots.

providing a pull wire for actuation of the non-tapered steering spine applying a tension force to the pull wire so that the non-tapered steering spine is maintained in a deflected state.

measuring a plurality of local radii of curvature ρ(x) of the non-tapered steering spine in the deflected state at known locations x, each of the plurality of local radii of curvature ρ(x) being measured at a respective location x along the longitudinal axis of the non-tapered steering spine, wherein x is measured from the proximal boundary of the proximal-most of the plurality of slots.

calculating an adjusted local radii of curvature ρa(x) according to Eq. (4).

repeating the step of calculating for different values of Δh/L until the adjusted local radii of curvature ρa(x) is uniform to within a desired tolerance.

It is further noted that, as used herein, the "beam thickness" of the tapered steering spine 40 corresponds only to the sections of the straight spine portion 50 that are between the rings 48. Accordingly, when the beam thickness is herein referred to as being "linear" or "non-linear," only the profile of the beam exclusive of the rings 48 are being described.

The invention may be practiced in other embodiments not disclosed herein. References to relative terms such as upper and lower, front and back, left and right, side, or the like, are intended for convenience of description and are not contemplated to limit the invention, or its components, to any specific orientation. All dimensions depicted in the figures may vary with a potential design and the intended use of a specific embodiment of this invention without departing from the scope thereof.

Each of the additional figures and methods disclosed herein may be used separately, or in conjunction with other features and methods, to provide improved devices, systems and methods for making and using the same. Therefore, combinations of features and methods disclosed herein may not be necessary to practice the invention in its broadest sense and are instead disclosed merely to particularly describe representative embodiments of the invention.

For purposes of interpreting the claims for the invention, it is expressly intended that the provisions of Section 112, sixth paragraph of 35 U.S.C. are not to be invoked unless the specific terms "means for" or "step for" are recited in the subject claim.

What is claimed is:

1. A tapered steering spine for a catheter system, comprising:
    a unitary body having a proximal end and a distal end and defining a longitudinal axis, said unitary body including a plurality of axially spaced rings that extend from a continuous and straight spine portion that runs along a same side of the tapered steering spine, said spine portion being parallel to said longitudinal axis,
    the axially spaced rings defining a plurality of slots along said length of said unitary body, each slot having a tangential dimension relative to said outer surface of said unitary body in a direction substantially orthogonal to said longitudinal axis, said tangential dimension of a first of said respective slots being greater than said tangential dimension of a second of said respective slots, said first of said respective slots being distal to said second of said respective slots; and
    a deflecting tab proximate the distal end of the tapered steering spine, said tab comprising first and second legs that are cantilevered from a distal end of the unitary body and extend proximally, wherein the proximal end of the legs are joined by an apex portion; and
    a stop portion that extends proximally from the distal end of the unitary body between the first and second legs, wherein a gap is defined between the apex portion and the proximal end of the stop portion, through which a hooked distal end of a pull wire is inserted.

2. The tapered steering spine of claim 1, wherein the pull wire is diametrically opposed to said spine portion to control tip deflection.

3. The tapered steering spine of claim 2 wherein said pull wire is mechanically fastened at said distal end of said unitary body.

4. The tapered steering spine of claim 1 wherein said tab is adapted to deflect inwardly in unison with the distal end portion of the pull wire upon insertion into a catheter shaft, said tab exerting a negligible reaction force on said catheter shaft.

5. The tapered steering spine of claim 1 further comprising a high lubricity coating that extends over at least a portion of said unitary body.

6. The tapered steering spine of claim 5 wherein said high lubricity coating is exclusive of portions of said unitary body near said proximal and distal ends to provide bonding surfaces for fixation of said unitary body to a catheter shaft.

7. A method of making a tapered steering spine for a catheter system, comprising:
    providing a unitary tube of a material defining a longitudinal axis;
    forming a plurality of slots in said unitary tube that are spaced axially along said length of said unitary tube to define a plurality of axially spaced rings that extend from a continuous and straight spine portion that runs along a same side of the tapered steering spine and in a direction that is lateral to said longitudinal axis, said axially spaced rings including structures that slidingly interlock with each other across a range of deflection of said continuous spine portion from a substantially straight orientation through a maximum deflection orientation to provide torsional rigidity while providing flexibility in a direction lateral to said longitudinal axis, wherein each of the axially spaced rings includes the structures that slidingly interlock with each other on a second side of each of the axially spaced rings that is diametrically opposed to the first side;
    providing a deflecting tab proximate a distal end of the tapered steering spine, the deflecting tab comprising first and second legs that are cantilevered from a distal end of the unitary tube and extend proximally, wherein the proximal end of the legs are joined by an apex portion;
    providing a stop portion that extends proximally from the distal end of the unitary body between the first and second legs, wherein a gap is defined between the apex portion and the proximal end of the stop portion;
    coating said unitary tube with a high lubricity coating; and
    affixing a catheter shaft to said unitary tube.

8. The method of making a tapered steering spine according to claim 7, wherein slots in said unitary tube are formed using laser cutting or electroerosion wire cutting.

9. The method of making a tapered steering spine according to claim 8, wherein said unitary tube provided in said step of providing is made of a nickel-titanium alloy.

10. The method of making a tapered steering spine according to claim 8, wherein said unitary tube provided in said step of providing is made of a nickel-cobalt alloy.

11. The method of making a tapered steering spine according to claim 8, wherein said unitary tube provided in said step of providing is made of spring steel.

12. The method of making a tapered steering spine according to claim 8, wherein said high lubricity coating provided in said step of coating does not extend over a length of said unitary tube near said proximal and distal ends of said unitary tube to provide bonding surfaces for affixing said catheter shaft to said unitary tube.

13. The method of making a tapered steering spine according to claim 8, wherein said high lubricity coating provided in said step of coating contains polytetrafluoroethylene, fluorinated ethylene propylene, or poly (p-xylylene) polymers.

14. A tapered steering spine for a catheter system, comprising:
   a unitary body of generally tubular shape having a proximal end and a distal end and defining a longitudinal axis, said unitary body including a plurality of axially spaced rings that extend from a continuous and straight spine portion that runs along a same side of the tapered steering spine, said spine portion being substantially parallel to said longitudinal axis;
   the plurality of axially spaced rings defining a plurality of slots along said length of said unitary body, each slot having a tangential dimension on said surface of said unitary body, said tangential dimension of said respective slots increasing from said proximal end to said distal end of said unitary body to provide increasing flexibility of said unitary body from said proximal end to said distal end;
   a single pull wire fastened at said distal end of said unitary body and diametrically opposed to said spine portion to control tip deflection from a substantially straight orientation through a maximum deflection orientation, wherein the single pull wire is fastened to a deflecting tab located proximate to the distal end of the tapered steering spine, the deflecting tab comprising first and second legs that are cantilevered from a distal end of the unitary tube and extend proximally, wherein the proximal end of the legs are joined by an apex portion; and
   a stop portion that extends proximally from the distal end of the unitary body between the first and second legs, wherein a gap is defined between the apex portion and the proximal end of the stop portion, through which a hooked distal end of the single pull wire is inserted.

15. A steering spine for a catheter system, comprising:
   a body having a proximal end and a distal end and defining a longitudinal axis, said body including a plurality of axially spaced rings that extend from a continuous spine portion that runs along a same side of the tapered steering spine, said continuous spine portion being parallel to said longitudinal axis, said continuous spine portion and said longitudinal axis being located in a steering plane of said steering spine, said axially spaced rings defining a plurality of slots along said length of said body, said axially spaced rings including structures that engage with complementary structures of adjacent rings, wherein the spine portion runs along a first side of each of the axially spaced rings, wherein each of the axially spaced rings includes the structures that engage with complementary structures on a second side of each of the axially spaced rings that is diametrically opposed to the first side, said structures and complementary structures being dimensioned to limit said minimum bend radius of said body when said body is flexed in a lateral direction away from said spine portion;
   wherein said body includes one or more laterally flexible regions, each region including at least one flexure, a first of said at least one flexure being in line with said continuous spine portion, said first flexure defining a perpendicular axis that is perpendicular to said longitudinal axis, said perpendicular axis being substantially in said steering plane;
   a deflecting tab proximate the distal end of the steering spine, comprising first and second legs that are cantilevered from a distal end of the unitary body and extend proximally, wherein the proximal end of the legs are joined by an apex portion; and
   a stop portion that extends proximally from the distal end of the unitary body between the first and second legs, wherein a gap is defined between the apex portion and the proximal end of the stop portion, through which a hooked distal end of a pull wire is inserted.

16. The steering spine of claim 15, wherein said at least one flexure includes a second flexure that is substantially at the same axial location as and in diametric opposition with said first flexure, said perpendicular axis passing through said first flexure and said second flexure.

17. The steering spine of claim 15, wherein at least one of said one or more laterally flexible regions includes an offset flexure pair that is rotationally offset with respect to said first flexure, the flexures of said offset flexure pair being in diametric opposition with each other.

18. The steering spine of claim 17 wherein said offset flexure pair is rotationally offset with respect to said first flexure by 90°.

19. The tapered steering spine of claim 15, wherein:
   the distal end portion of the pull wire is coupled to a proximal end of the deflecting tab; and
   a passage is defined through a wall of the body that borders a proximal end of the apex portion, the passage configured to enable a portion of the hooked distal end of the pull wire to pass through as the deflecting tab and the pull wire are deflected inward.

* * * * *